US00RE46953E

(19) United States
(12) Reissued Patent
Yu et al.

(10) Patent Number: US RE46,953 E
(45) Date of Reissued Patent: Jul. 17, 2018

(54) SINGLE-ARC DOSE PAINTING FOR PRECISION RADIATION THERAPY

(71) Applicants: University of Maryland, Baltimore, Baltimore, MD (US); STC.UNM, Albuquerque, NM (US); University of Notre Dame du Lac, Notre Dame, IN (US)

(72) Inventors: Cedric X. Yu, Clarksville, MD (US); Shuang Luan, Albuquerque, NM (US); Danny Z. Chen, Granger, IN (US); Matthew A. Earl, Edgewater, MD (US); Chao Wang, Columbia, MD (US)

(73) Assignees: UNIVERSITY OF MARYLAND, BALTIMORE, Baltimore, MD (US); UNIVERSITY OF NOTRE DAME DU LAC, Notre Dame, IN (US); STC.UNM, Albuquerque, NM (US)

(21) Appl. No.: 14/020,500

(22) Filed: Sep. 6, 2013

Related U.S. Patent Documents

Reissue of:
(64) Patent No.: 8,014,494
Issued: Sep. 6, 2011
Appl. No.: 12/589,205
Filed: Oct. 20, 2009

U.S. Applications:
(63) Continuation of application No. PCT/US2008/005028, filed on Apr. 18, 2008.
(Continued)

(51) Int. Cl.
*A61N 5/10* (2006.01)
*G21K 1/02* (2006.01)
*H05G 1/42* (2006.01)

(52) U.S. Cl.
CPC ..... *A61N 5/1047* (2013.01); *A61N 5/1036* (2013.01)

(58) Field of Classification Search
CPC .... A61N 5/103; A61N 5/1067; A61N 5/1031; A61N 5/1082; A61N 5/10; A61N 5/1038; A61N 5/1048; A61N 2005/1062
(Continued)

(56) References Cited

U.S. PATENT DOCUMENTS 3,133,227 A 5/1964 Brown et al.
3,144,552 A 8/1964 Schonberg et al.
(Continued)

FOREIGN PATENT DOCUMENTS

AU 746987 B2 2/2000
AU 2002215340 B2 4/2002
(Continued)

OTHER PUBLICATIONS

Bortfeld, et al. X-Ray Field Compensation with Multileaf Collimaters, Int. J. Radiation Oncology Biol. Phys. vol. 28, No. 3, pp. 723-730, 1994.
(Continued)

*Primary Examiner* — Catherine S. Williams
(74) *Attorney, Agent, or Firm* — Benjamin Aaron Adler

(57) ABSTRACT

Provided herein are methods and systems for designing a radiation treatment for a subject using single arc dose painting. The methods and systems comprise an algorithm or a computer-readable product having the same, to plan the radiation treatment. The algorithm converts pairs of multiple leaf collimation (MLC) leaves to sets of leaf aperture sequences that form a shortest path single arc thereof where the pairs of MLC leaves each aligned to an intensity profile of densely-spaced radiation beams, and connects each single arc of leaf apertures to form a final treatment single arc. Also provided is a method for irradiating a tumor in a subject using single arc dose painting.

45 Claims, 11 Drawing Sheets

Related U.S. Application Data

(60) Provisional application No. 60/913,175, filed on Apr. 20, 2007.

(58) Field of Classification Search
USPC ..... 378/65, 97, 64, 95, 108, 147–153
See application file for complete search history.

(56) References Cited

U.S. PATENT DOCUMENTS 3,193,717 A 7/1965 Nunan
3,906,233 A 9/1975 Vogel
3,987,281 A 10/1976 Hodes
4,149,247 A 4/1979 Pavkovich et al.
4,149,248 A 4/1979 Pakovich
4,208,675 A 6/1980 Bajon et al.
4,209,706 A 6/1980 Nunan
4,521,808 A 6/1985 Ong et al.
4,547,892 A 10/1985 Richey et al.
4,593,967 A 6/1986 Haugen
4,628,523 A 12/1986 Heflin
4,675,731 A 6/1987 Takasu et al.
4,679,076 A 7/1987 Vikterlof et al.
4,726,046 A 2/1988 Nunan
4,741,621 A 5/1988 Taft et al.
4,825,393 A 4/1989 Nishiya
4,853,777 A 8/1989 Hupp
4,868,843 A 9/1989 Nunan
4,868,844 A 9/1989 Nunan
5,001,344 A 3/1991 Kato et al.
5,014,292 A 5/1991 Siczek et al.
5,027,818 A 7/1991 Bova et al.
5,039,867 A 8/1991 Nishihara et al.
5,080,100 A 1/1992 Trotel
5,099,505 A 3/1992 Seppi et al.
5,117,445 A 5/1992 Seppi et al.
5,157,707 A 10/1992 Ohlson
5,168,532 A 12/1992 Seppi et al.
5,207,223 A 5/1993 Adler
5,247,555 A 9/1993 Moore et al.
5,262,649 A 11/1993 Antonuk et al.
5,332,908 A 7/1994 Weidlich
5,335,255 A 8/1994 Seppi et al.
5,394,452 A 2/1995 Swerdloff et al.
5,400,255 A 3/1995 Hu
5,411,026 A 5/1995 Carol
5,427,097 A 6/1995 Depp
5,438,991 A 8/1995 Yu et al.
5,442,675 A 8/1995 Swerdloff et al.
5,471,516 A 11/1995 Nunan
5,471,546 A 11/1995 Meier
5,509,042 A 4/1996 Mazess
5,521,957 A 5/1996 Hansen
5,537,452 A 7/1996 Shepherd et al.
5,591,983 A 1/1997 Yao
5,647,663 A 7/1997 Holmes
5,661,773 A 8/1997 Swerdloff et al.
5,663,995 A 9/1997 Hu
5,663,999 A 9/1997 Siochi
5,673,300 A 9/1997 Reckwerdt et al.
5,675,625 A 10/1997 Rockseisen
5,692,507 A 12/1997 Seppi et al.
5,719,914 A 2/1998 Rand et al.
5,724,400 A 3/1998 Swerdloff et al.
5,727,554 A 3/1998 Kalend et al.
5,748,700 A 5/1998 Shepherd et al.
5,748,703 A 5/1998 Cosman
5,751,781 A 5/1998 Brown et al.
5,757,881 A 5/1998 Hughes
5,802,136 A 9/1998 Carol
5,818,902 A 10/1998 Yu et al.
5,835,558 A 11/1998 Maschke
5,848,126 A 12/1998 Fujita et al.
5,858,891 A 1/1999 Auzel et al.
5,877,501 A 3/1999 Ivan et al.
5,912,943 A 6/1999 Deucher
5,926,521 A 7/1999 Tam
5,929,449 A 7/1999 Huang
5,949,811 A 9/1999 Baba et al.
5,956,382 A 9/1999 Wiener-Avnear et al.
5,960,055 A 9/1999 Samarasekera et al.
5,999,587 A 12/1999 Ning et al.
6,031,888 A 2/2000 Ivan et al.
6,038,283 A 3/2000 Carol et al.
6,041,097 A 3/2000 Roos et al.
6,052,430 A 4/2000 Siochi et al.
6,075,836 A 6/2000 Ning
6,078,638 A 6/2000 Sauer et al.
6,104,778 A 8/2000 Murad
6,104,780 A 8/2000 Hanover et al.
6,108,400 A 8/2000 Siochi
6,113,264 A 9/2000 Watanabe
6,134,296 A 10/2000 Siochi
6,142,925 A 11/2000 Siochi et al.
6,144,875 A 11/2000 Schweikard et al.
6,148,058 A 11/2000 Dobbs
6,152,598 A 11/2000 Tomisaki et al.
6,200,024 B1 3/2001 Negrelli
6,219,403 B1 4/2001 Nishihara
6,219,441 B1 4/2001 Hu
6,222,901 B1 4/2001 Meulenbrugge et al.
6,240,161 B1 5/2001 Siochi
6,256,366 B1 7/2001 Lai
6,260,005 B1 7/2001 Yang et al.
6,269,141 B1 7/2001 Proksa et al.
6,269,143 B1 7/2001 Tachibana
6,278,766 B1 8/2001 Kooy et al.
6,285,739 B1 9/2001 Rudin et al.
6,292,526 B1 9/2001 Patch
6,307,914 B1 10/2001 Kunieda et al.
6,314,159 B1 11/2001 Siochi
6,318,892 B1 11/2001 Suzuki et al.
6,325,537 B1 12/2001 Watanabe
6,325,758 B1 12/2001 Carol et al.
6,330,300 B1 12/2001 Siochi
6,335,961 B1 1/2002 Wofford et al.
6,345,114 B1 2/2002 Mackie et al.
6,349,129 B1 2/2002 Siochi
6,353,222 B1 3/2002 Dotan
6,370,421 B1 4/2002 Williams et al.
6,381,302 B1 4/2002 Berestov
6,385,286 B1 5/2002 Fitchard et al.
6,385,288 B1 5/2002 Kanematsu
6,385,477 B1 5/2002 Werner et al.
6,393,096 B1 5/2002 Carol et al.
6,411,675 B1 6/2002 Llacer
6,429,578 B1 8/2002 Danielsson et al.
6,435,715 B1 8/2002 Betz
6,438,202 B1 8/2002 Olivera et al.
6,445,766 B1 9/2002 Whitham et al.
6,463,122 B1 10/2002 Moore
6,473,490 B1 10/2002 Siochi
6,480,565 B1 11/2002 Ning
6,504,892 B1 1/2003 Ning
6,504,899 B2 1/2003 Pugachev et al.
6,508,586 B2 1/2003 Oota
6,546,073 B1 4/2003 Lee et al.
6,560,311 B1 5/2003 Shepard et al.
6,582,121 B2 6/2003 Crain
6,590,953 B2 7/2003 Suzuki et al.
6,661,870 B2 12/2003 Kapatoes et al.
6,661,872 B2 12/2003 Bova
6,714,620 B2 3/2004 Caflisch et al.
6,735,277 B2 5/2004 McNutt et al.
6,741,674 B2 5/2004 Lee
6,744,848 B2 6/2004 Stanton et al.
6,757,355 B1 * 6/2004 Siochi ..... 378/65
6,760,402 B2 7/2004 Ghelmansarai
6,792,074 B2 9/2004 Erbel et al.
6,813,336 B1 11/2004 Siochi
6,842,502 B2 1/2005 Jaffray et al.
6,850,252 B1 2/2005 Hoffberg
6,852,974 B2 2/2005 Kochi et al.
6,853,705 B2 2/2005 Chang
6,865,254 B2 3/2005 Nafstadius

(56) References Cited

U.S. PATENT DOCUMENTS 6,888,919 B2 3/2005 Graf
6,879,659 B2 4/2005 Alber
6,882,702 B2 4/2005 Luo
6,907,105 B2 * 6/2005 Otto ..... 378/65
6,914,959 B2 7/2005 Bailey et al.
6,934,653 B2 8/2005 Ritt
6,937,693 B2 8/2005 Svatos
6,968,035 B2 11/2005 Siochi
6,990,175 B2 1/2006 Nakashima
7,030,386 B2 4/2006 Pang
7,046,762 B2 5/2006 Lee
7,085,348 B2 8/2006 Kamath et al.
7,096,055 B1 8/2006 Schwelkard
7,151,258 B2 12/2006 Kochi et al.
7,162,008 B2 1/2007 Earl et al.
7,180,980 B2 2/2007 Nguyen
7,221,733 B1 5/2007 Takai et al.
7,227,925 B1 6/2007 Mansfield et al.
7,329,867 B2 2/2008 Kochi et al.
7,333,591 B2 2/2008 Earl et al.
7,346,144 B2 3/2008 Hughes et al.
7,349,522 B2 3/2008 Yan et al.
7,352,370 B2 4/2008 Wang et al.
7,369,645 B2 5/2008 Lane
7,438,685 B2 10/2008 Burdette et al.
7,471,765 B2 12/2008 Jaffray et al.
7,525,090 B1 4/2009 Krzeczowski
7,529,599 B1 5/2009 Bhatt et al.
7,556,596 B2 7/2009 Mourtada et al.
7,657,304 B2 2/2010 Mansfield et al.
7,693,683 B2 4/2010 Ihara
7,755,043 B1 7/2010 Gubbens
7,813,822 B1 10/2010 Hoffberg
7,826,592 B2 11/2010 Jaffray et al.
7,831,289 B2 11/2010 Riker et al.
7,872,236 B2 1/2011 Zhang
7,880,154 B2 2/2011 Otto et al.
7,881,772 B2 2/2011 Ghelmansarai
7,906,770 B2 3/2011 Otto et al.
7,907,987 B2 3/2011 Dempsey
7,945,021 B2 5/2011 Shapiro et al.
7,961,843 B2 5/2011 Brown et al.
8,116,430 B1 2/2012 Shapiro et al.
8,696,538 B2 4/2014 Otto et al.
8,788,020 B2 7/2014 Mostafavi et al.
2001/0001807 A1 5/2001 Green
2001/0008271 A1 7/2001 Ikeda et al.
2002/0006182 A1 1/2002 Kim et al.
2002/0066860 A1 6/2002 Possin
2002/0179812 A1 12/2002 Kochi et al.
2003/0007601 A1 1/2003 Jaffray et al.
2003/0086530 A1 5/2003 Otto
2003/0212325 A1 11/2003 Cortrutz et al.
2003/0219098 A1 11/2003 McNutt et al.
2004/0001569 A1 1/2004 Luo
2004/0022438 A1 2/2004 Hibbard
2004/0071261 A1 * 4/2004 Earl ..... A61N 5/1031 378/65
2004/0116804 A1 6/2004 Mostafavi et al.
2004/0120452 A1 6/2004 Shapiro et al.
2004/0165696 A1 * 8/2004 Lee ..... A61N 5/1031 378/65
2004/0190680 A1 9/2004 Chang
2004/0254448 A1 12/2004 Amies et al.
2005/0040332 A1 2/2005 Kochi et al.
2005/0061972 A1 3/2005 Kochi et al.
2005/0096515 A1 5/2005 Geng
2005/0111621 A1 5/2005 Riker et al.
2005/0148841 A1 * 7/2005 Kamath ..... A61N 5/103 600/407
2005/0197564 A1 9/2005 Dempsey
2006/0060780 A1 3/2006 Masnaghetti et al.
2006/0176295 A1 8/2006 Toho et al.
2006/0235260 A1 10/2006 Mourtada et al.
2006/0256915 A1 * 11/2006 Otto ..... A61N 5/1031 378/65
2006/0274061 A1 12/2006 Wang et al.
2006/0274925 A1 12/2006 West et al.
2006/0289757 A1 12/2006 Kochi et al.
2007/0220108 A1 9/2007 Whitaker
2007/0221842 A1 9/2007 Morokuma et al.
2007/0230770 A1 10/2007 Kulkarni et al.
2007/0242797 A1 10/2007 Stewart et al.
2008/0114564 A1 5/2008 Ihara
2008/0226030 A1 9/2008 Otto
2008/0298550 A1 12/2008 Otto
2008/0317330 A1 12/2008 Takeda et al.
2009/0161827 A1 6/2009 Gertner et al.
2009/0207975 A1 * 8/2009 Bourne ..... 378/150
2009/0213991 A1 * 8/2009 Brown et al. ..... 378/65
2009/0220046 A1 * 9/2009 Ji et al. ..... 378/65
2009/0230304 A1 9/2009 Hatano et al.
2009/0297019 A1 12/2009 Zafar et al.
2009/0322973 A1 12/2009 Ito et al.
2010/0020931 A1 1/2010 Otto et al.
2010/0054410 A1 * 3/2010 Nord et al. ..... 378/65
2011/0012911 A1 1/2011 Nakamura et al.

FOREIGN PATENT DOCUMENTS

DE 3828639 A1 3/1989
DE 4223488 A1 1/1994
DE 19614643 A1 10/1997
DE 69319010 T2 10/1998
DE 19800946 A1 7/1999
DE 19931243 A1 2/2000
DE 10139934 A1 3/2003
DE 10305421 A1 8/2004
EP 0062941 A1 10/1982
EP 0062941 B1 9/1984
EP 0205720 A1 12/1986
EP 0480035 A1 4/1992
EP 0480035 B1 11/1994
EP 480035 B1 11/1994
EP 713677 A1 5/1996
EP 656797 B1 9/1998
EP 0922943 A2 6/1999
EP 0948930 A1 10/1999
EP 810006 B1 8/2000
EP 1095628 A2 5/2001
EP 965104 B1 9/2001
EP 471455 A2 4/2002
EP 989886 B1 9/2004
EP 814869 B1 12/2004
EP 1165182 B1 3/2005
EP 948930 B1 9/2007
EP 1318857 B1 7/2008
EP 1308185 B1 12/2010
EP 1383427 B1 3/2011
EP 1525902 B1 4/2015
EP 1397700 B1 7/2015
FR 2269745 A1 4/1974
FR 2269745 A1 11/1975
FR 2551664 A1 9/1983
FR 2551664 A1 3/1985
GB 1328033 A 8/1973
JP 59000076 A 1/1984
JP 1040069 A 2/1989
JP H01162682 A 6/1989
JP 0557028 A 3/1993
JP 5057028 A 3/1993
JP 200679006 A 3/1994
JP 2006339541 A 12/1994
JP 07255717 A 10/1995
JP 9239044 A 9/1997
JP 10113400 A 5/1998
JP 10328318 A 12/1998
JP S63294839 A 12/1998
JP 1199148 A 4/1999
JP 11160440 A 6/1999
JP 2000116638 A 4/2000
JP 2000140137 A 5/2000
JP 2000152927 A 6/2000

(56) References Cited

FOREIGN PATENT DOCUMENTS

| | | | |
|---|---|---|---|
| JP | 2000317000 | A | 11/2000 |
| JP | 2001029489 | A | 2/2001 |
| JP | 2001029491 | A | 2/2001 |
| JP | 2001120528 | A | 5/2001 |
| JP | 2001095793 | A | 10/2001 |
| JP | 2004097646 | A | 4/2004 |
| JP | 2004166975 | A | 6/2004 |
| JP | 2004194697 | A | 7/2004 |
| JP | 2008163575 | A | 7/2008 |
| JP | 5894835 | B2 | 3/2016 |
| WO | 198503212 | A1 | 8/1985 |
| WO | 1990014129 | A1 | 11/1990 |
| WO | 1992000567 | A1 | 1/1992 |
| WO | 92002277 | A1 | 2/1992 |
| WO | 1992020202 | A1 | 11/1992 |
| WO | 95000204 | A1 | 1/1995 |
| WO | 9713552 | A1 | 4/1997 |
| WO | 9742522 | A1 | 11/1997 |
| WO | 9852635 | A1 | 11/1998 |
| WO | 9903397 | A1 | 1/1999 |
| WO | 199948558 | A1 | 9/1999 |
| WO | 200015299 | A1 | 3/2000 |
| WO | 200160236 | A2 | 8/2001 |
| WO | 2002013907 | A1 | 2/2002 |
| WO | 2003003796 | A1 | 2/2002 |
| WO | 2002024277 | A1 | 3/2002 |
| WO | 02061680 | A2 | 8/2002 |
| WO | 03008986 | A2 | 1/2003 |
| WO | 2005057738 | A1 | 1/2003 |
| WO | 2003099380 | A1 | 12/2003 |
| WO | 2005057738 | A2 | 6/2005 |

OTHER PUBLICATIONS

Boyer, A.L. and Yu, C.X. Intensity-Modulated Radiation Therapy with Dynamic Multileaf Collimators, Seminars in Radiation Oncology, vol. 9, No. 1, pp. 48-59, Jan. 1999.
Braime, Anders, Individualizing Cancer Treatment: Biological Optimization Models in Treatment Planning and Delivery, Int. J. Radiation Oncology Biol. Phys, vol. 49, No. 2, pp. 327-337, 2001.
Bzdusek et al. Development and Evaluation of an Efficient Approach to Volumetric Arc Therapy Planning, Med Phys, vol. 36, No. 6, pp. 2328-2339, Jun. 2009.
Cameron, C., Sweeping-Window Arc Therapy: An Implementation of Rotational IMRT with Automatic Beam-Weight Calculation, Phys. Med. Biol., vol. 50, pp. 4317-4336, 2005.
Cho, P.S. and Marks II, R.J., Hardware-Sensitive Optimization for Intensity Modulated Radiotherapy, Phys. Med. Biol., vol. 45, pp. 429-440, 2000.
Earl et al. Inverse Planning for Intensity-Modulated Arc Therapy Using Direct Aperture Optimization, Phy. Med. Biol., vol. 48, pp. 1075-1089, 2003.
Mackie et al. Tomotherapy: A New Concept for the Delivery of Dynamic Conformal Radiotherapy, Med. Phys., vol. 20, No. 6, pp. 1709-1719, Nov./Dec. 1993.
Shepard et al. Iterative Approaches to Dose Optimization in Tomotherapy, Phys. Med. Biol. vol. 45, pp. 69-90, 2000.
Shepard et al. An Arc-Sequencing Algorithm for Intensity Modulated Arc Therapy, Med. Phys., vol. 34, No. 2, pp. 464-470, Feb. 2007.
Webb, Optimizing the Planning of Intensity-Modulated Radiotherapy, Phys. Med. Biol. vol. 39, pp. 2229-2246, 1994.
Yu, C.X., Intensity-Modulated Arc Therapy with Dynamic Multileaf Collimation: An Alternative to Tomotherapy, hys. Med. Biol., vol. 40, pp. 1435-1449, 1995.
Yu et al. Clinical Implementation of Intensity-Modulated Arc Therapy, Int. J. Radiation Oncology Biol. Phys, vol. 53, No. 2, pp. 453-463, 2002.
Qiuwen, Wu et al., Dynamic Splitting of Large Intensity-Modulated Fields, Phys. Med. Biol. 45 (2000), Richmond, VA, USA, p. 1731-1740.
Gerard Verfaillie et al., Russian Doll Search for Solving Constraint Optimization Problems, AAAI-96 Proceedings, 1996, p. 181-187.
BrainLAB New Gating System from BrainLAB Enables Breakthrough in the Radiotherapy Treatment of Lung and Liver Patients, Sep. 28, 2004, 4 pages.
Graham Carey, Computational Grids Generational, Adaptation and Solution Strategies, The University of Texas, Austin, Texas, 1997.
D. Verellen et al., A (short) history image-guided radiotherapy, Radiotherapy & Oncology, vol. 86, 2008, p. 4-13.
M. Van Herk et al., Automatic three-dimensional correlation of CT-CT, CT-MRI, and CT-SPECT using chamfer matching, Medical Physics, 1994, p. 1163-1178.
R.P. Woods et al., MRI-PET Registration with Automated Algorithm, Journal of Computer Assisted Tomography, 1993, p. 536-546.
Jaffray et al., A Volumentric Cone-Beam CT System Based on a 41×41 cm2 Flat-Panel Imager, 2001, p. 800-807.
Otto, K, Intensity Modulation of Therapeutic Photon Beams Using a Rotating Multileaf Collimator, 2004, vol. 31 (3), p. 686.
Lim, J., Optimization in Radiation Treatment Planning, 2002.
Mueller, K. et al., Cone-Beam Computed Tomography (CT) for a Megavoltage Linear Accelerator (LINAC) Using an Electronic Portal Imaging Device (EPID) and the Algebraic Reconstruction Technique (ART), 2000, p. 2875-2878.
Nag, S., et al., Intraoperative Planning and Evaluation of Permanent Prostate Brachytherapy: Report of the American Brachytherapy Society, 2001, p. 1422-1430.
Munro, P., Portal Imaging Technology: Past, Present, and Future, Seminars in Radiation Oncology, 1995, p. 115-133.
De Neve, W., et al., Routine clinical on-line portal imaging followed by immediate field adjustment using a tele-controlled patient couch, 1992, p. 45-54.
Antonuk, L.E. et al., Thin-Film, Flat-Panel, Composite Imagers for Projection and Tomographic Imaging, IEEE Transactions on Medical Imaging, 1994, p. 482-490.
Sephton, R., et al., A diagnostic-quality electronic portal imaging system, 1995, p. 204-247.
Kirby, M.C. et al., Clinical Applications of Composite and Realtime Megavoltage Imaging, 1995, p. 308-316.
Webb, S. et al., Tomographic Reconstruction from Experimentally Obtained Cone-Beam Projections, 1987, p. 67-73.
Midgley, S.M. et al., A Feasibility Study for the Use of Megavoltage Photons and a Commercial Electronic Portal Imaging Area Detector for Beam Geometry CT Scanning to Obtain 3D Tomographic Data Sets of Radiotherapy Patients in the Treatment Position, 1996, 2 pages.
Antonuk, L.E. et al., Demonstration of megavoltage and diagnostic x-ray imaging with hydrogenated amorphous silicon arrays, 1992, p. 1455-1466.
Chabbal, J. et al., Amorphous Silicon X-ray Image Sensor, 1996, p. 499-510.
Ning, R. et al., Selenium Flat Panel Detector-Based Volume Tomographic Angiography Imaging: Phantom Studies, 1998, p. 316-324.
Redpath, A.T. et al., Chapter 6: Simulator Computed Tomography, The Modern Technology of Radiation Oncology, 1999, pp. 169-189.
Boyer et al., Laser "Cross-hair" sidelight, 1978, p. 58-60.
Jaffray et al., Image Guided Radiotherapy of the Prostate, 2001, p. 1075-1080.
MacKenzie, M. et al., Intensity modulated arc deliveries approximated by a large number of fixed gantry position sliding window dynamic multileaf collimator fields, 2002, p. 2359-2365.
Bissonnette, J-P et al., An Alternative X-Ray Detector for Portal Imaging: High Density Glass Scintillator, 1993, p. 36-37.
Bissonnette, J-P et al., Physical characterization and optimal magnification of a portal imaging system, 1992, p. 182-188.
Colbeth, R. et al., 40×30 cm Flat Panel Imager for Angiography, R&F, and Cone-Beam CT Applications, 2001, p. 94-102.
Colbeth, R. et al., Characterization of an Amorphous Silicon Fluoroscopic Imager, 1997, p. 42-51.
Colbeth, R. et al., Characterization of a third generation, multi-mode sensor panel, 1999, p. 491-500.
Colbeth, R. et al., A Multi-mode X-ray Imager for Medical and Industrial Applications, 1998, p. 629-632.

(56) References Cited

OTHER PUBLICATIONS

Colbeth, R. et al., Flat panel imaging system for fluoroscopy applications, 1998, p. 376-387.
Gilblom, D. et al., Real-time x-ray imaging with flat panels, 1998, p. 213-223.
Gilblom, D. et al., A real-time, high-resolution camera with an amorphous silicon large-area sensor, 1998, p. 29-38.
Jaffray, D. et al., Medical linear accelerator x-ray sources: Variation with make, model, and time, 1992, p. 174-181.
Klausmeier-Brown, M.E. et al., Real-Time Image Processing in a Flat-Panel, Solid-State, Medical Fluoroscopic Imaging System, 1998, p. 2-7.
Kubo, H., Potential and role of a prototype amorphous silicon array electronic portal imaging device in breathing synchronized radiotherapy, 1999, p. 2410-2414.
Munro, P. et al., A Digital Fluoroscopic Imaging Device for Radiotherapy Localization, 1990, p. 641-649.
Ning, R. et al., Real Time Flat Panel Detector-Based Volume Tomographic Angiography Imaging: Detector Evaluation, 2000, p. 396-407.
Munro P., et al., Therapy imaging• limitations of imaging with high energy x-ray beams, 1987, p. 178-184.
Wright, M. et al., Amorphous silicon dual mode medical imaging system, 1998, p. 505-514.
Cho, Y., et al., Thermal Modelling of a Kilovoltage X-Ray Source for Portal Imaging, 2000, p. 1856-1860.
Zheng, Z, et al., Fast 4D Cone-Beam Reconstruction Using the McKinnon-Bates Algorithm with Truncation Correction and Non Linear Filtering, , 2011, p. 1-8.
Elbert, M. et al., 3D image guidance in radiotherapy: a feasibility study, 2001, p. 1807-1816.
Ford, E.C. et al., Cone-beam CT with megavoltage beams and an amorphous silicon electronic portal imaging device: Potential for verification of radiotherapy of lung cancer, 2002, p. 2913-2924.
Hunt, P. et al., Development of an IMRT quality assurance program using an amorphous silicon electronic portal Imaging device, 2000, 1 page.
Johnsen, S. et al., "Improved Clinac Electron Beam Quality", 1983, p. 737.
Wong, J. et al., "Initial clinical experience with a gantry mounted dual beam imaging system for setup error localization", 1998, p. 138.
Munro, P. et al., "Megavoltage Cone-Beam Computed Tomography Using a High Quantum Efficiency Image Receptor", 2002, p. 1340.
Performance of a Volumetric CT Scanner Based Upon a Flat-Panel Imager, D. Jaffray, J. Siewersen, D. Drake, Feb. 1999, pp. 204-214.
Flat-Panel Cone-Beam CT on a Mobile Isocentric C-Arm for Image-Guided Brachytherapy, D. Jaffray, J. Siewerdsen, G. Edmundson, J. Wong, A. Martinez, 2002, pp. 209-217.
Cone-beam computed tomography with a flat-panel imager: Initial performance characterization, D. Jaffray, J. Siewerdsen, Jun. 2000, pp. 1311-1323.
A Radiographic and Tomographic Imaging System Integrated into a Medical Linear Accelerator for Localization of a Bone and Soft-Tissue Targets, D. Jaffray, D. Drake, M. Moreau, A. Martinez, J. Wong, 1999, pp. 773-789.
Cone-beam computed tomography with a flat-panel imager: Effects of image lag, J. Siewerdsen, D. Jaffray, 1999, pp. 2635-2647.
Cone-Beam CT with a Flat-Panel Imager: Noise Considerations for Fully 3-D Computed Tomography, J. Siewerdsen, D. Jaffray, 2000, pp. 408-416.
Optimization of x-ray imaging geometry (with specific application to flat-panel cone—beam computed tomography), J. Siewerdsen, D. Jaffray, Aug. 2000, pp. 1903-1914.
Adaptive Modification of Treatment Planning to Minimize the Deleterious Effects of Treatment Setup Errors, D. Yan, J. Wong, F. Vicini, J. Michalski, C. Pan, A. Frazier, E. Horwitz, A. Martinez, 1997, pp. 197-206.
Intensity Modulated Arc Therapy: Technology and Clinical Implementation, C. Yu, Sep. 1995, pp. 1-14.
Elements of X-Ray Diffraction, Cullity B., 1978, pp. 6-12.
Intensity modulated arc therapy (IMAT) with centrally blocked rotational fields, C. Cotrutz, C. Kappas, S. Webb, 2000, pp. 2185-2206.
Clinical Implementation of Intensity-Modulated Arc Therapy (IMAT) for Rectal Cancer, W. Duthoy, W. De Gersem, K. Vergote, T. Boterberg, C. Derie, P. Smeets, C. Wagter, W. De Neve, 2004, pp. 794-806.
Systematic verification of a three-dimensional electron beam dose calculation algorithm, Cheng A. et al., 1996, pp. 685-693.
Intensity-Modulated Arc Therapy Simplified, E. Wong, J. Chen, J. Greenland, 2002, pp. 222-235.
Intensity-Modulated Arc Therapy for Treatment of High-Risk Endometrial Malignancies, E. Wong, D. D'Souza, J. Chen, M. Lock, G. Rodrigues, T. Coad, K. Trenka, M. Mulligan, G. Bauman, 2005, pp. 830-841.
Three-Dimensional Photon Treatment Planning for Hodgkin's Disease, Brown A. et al., May 1992, pp. 205-215.
Optimized Intensity-modulated Arc Therapy for Prostate Cancer Treatment, L. Ma, C. Yu, M. Earl, T. Holmes, M. Sarfaraz, X. Li, D. Shepard, P. Amin, S. DiBiase, M. Suntharalingam, C. Mansfield, 2001, pp. 379-384.
Synchronized moving aperture radiation therapy (SMART): average tumour trajectory for lung patients, T. Neicu, H. Shirato, Y. Seppenwoolde, S. Jiang, 2003, pp. 587-598.
Aperture modulated arc therapy, S. Crooks, X.Wu, C. Takita, M. Watzich, L. Xing, 2003, pp. 1333-1344.
Automated selection of beam orientations and segmented intensity-modulated radiotherapy (IMRT) for treatment of oesophagus tumors, E. Woudstra, B. Heijmen, P. Storchi, 2005, pp. 254-261.
A review of electronic portal imaging devices, Boyer A et al., 1992, pp. 1-16.
Inverse Bestrahlungsplanung fuer intensitaetsmodulierte Strahlenfelder mit Linearer Programmierung als Optimierungsmethode, Matthias Hilbig, 2003, 156 pages.
Entwicklung eines inversen Bestrahlungsplans mit linearer Optimierung, Matthias Hilbig; Robert Hanne; Peter Kneschaurek; Frank Zimmermann, Achim Schweikard, 2002, v. 12, pp. 89-96.
Fluenzmodulierte Strahlentherapie mit in die Optimierung integrierter Segmentierung, Werner Baer; Markus Alber; Fridtjof Nuesslin, 2003, v. 13, pp. 12-15.
Methods of mathematical simulation and planning of fractionated irradiationof malignant tumors, Klepper L. Ya., Sotnikov V.M., Zamyatin O.A., Nechesnyuk A.V., 2000, v. 2, pp. 73-79.
Accuracy improvement of irradiation position and new trend, Nakagawa T., et al., 2001, pp. 102-105.
X-ray detector in IT era—FPD : Flat Panel Detector, Nishiki M., 2001, pp. 1-2.
Development of corn beam X-ray CT system, Watanabe Y., Oct. 2002, pp. 778-783.
The Stanford medical linear accelerator. II. Installation and physical measurements, Weissbluth, M., C. J. Karzmark et al., 1959, pp. 242-253.
A diagnostic X ray field verification device for a 10 MV linear accelerator, Biggs PJ,Goitein M,Russell MD, Mar. 1985, pp. 635-643.
New Patient Set Up in Linac-CT Radiotherapy System—First Mention of a Hybrid CT-Linac System, Akanuma, A., et al., 1984, pp. 465-467.
A dual computed tomography linear accelerator unit for stereotactic radiation therapy: a new approach without cranially fixated stereotactic frames, Uematsu M, Fukui T, Shioda A, Tokumitsu H, Takai K, Kojima T, Asai, Jun. 1, 1996, pp. 587-592.
Tomotherapy: a new concept for the delivery of dynamic conformal radiotherapy, Mackie TR, Holmes T, Swerdloff S, Reckwerdt P, Deasy JO, Yang J, Paliwal, 1993, pp. 1709-1719.
A room-based diagnostic imaging system for measurement of patient setup, Schewe JE, Lam KL, Baiter JM, Ten Haken RK, Dec. 1998, pp. 2385-2387.
Initial Performance Evaluation of an Indirect-Detection, Active Matrix Flat-Panel Imager (AMFPI) Prototype for Megavoltage Imaging, Antonuk L, et al., 1998, pp. 661-672.

(56) References Cited

OTHER PUBLICATIONS

Megavoltage Imaging with a Large-Area, Flat-Panel, Amorphous Silicon Imager, Antonuk L, et al., 1996, pp. 661-672.
A Real-Time, Flat-Panel, Amorphous Silicon, Digital X-ray Imager, Antonuk L, et al., Jul. 1995, pp. 993-1000.
Strategies to improve the signal and noise performance of active matrix, flat-panel imagers for diagnostic x-ray applications, Antonuk L. et al., Feb. 2000, pp. 289-306.
An Interactive Computer System for Studying Human Mucociliary Clearance, Bassett P., 1979, pp. 97-105.
Optimal radiographic magnification for portal imaging, Bissonnette J. et al.,1994, pp. 1435-1445.
Intensity-Modulated Radiotherapy: Current Status and Issues of Interest, Boyer A et al., 2001, pp. 880-914.
Ion Beam Sputter-Deposited SiN/TiN Attenuating Phase-Shift Photoblanks, Dieu L. et al., 2001, pp. 810-817.
A Multileaf Collimator Field Prescription Preparation System for Conventional Radiotherapy, Du M. et al., 1994, pp. 707-714.
A Multileaf Collimator Field Prescription Preparation System for Conventional Radiotherapy, Du M. et al., 1995, pp. 513-520.
Relative dosimetry using active matrix flat-panel imager (AMFPI) technology, El-Mohri Y. et al., 1999, pp. 1530-1541.
Daily Monitoring and Correction of Radiation Field Placement Using a Video-Based Portal Imaging System: A Pilot Study, Ezz A. et al., 1991, pp. 159-165.
Dosimetric Evaluation of the Conformation of the Multileaf Collimator to Irregularly Shaped Fields, Frazier A. et al., 1995, pp. 1229-1238.
Effects of Treatment Setup Variation on Beam's Eye View Dosimetry for Radiation Therapy Using the Multileaf Collimator vs. the Cerrobend Block, Frazier A. et al., 1995, pp. 1247-1256.
A Method to Analyze 2-Dimensional Daily Radiotherapy Portal Images from an On-Line Fiber-Optic Imaging System, Graham M. et al., 1991, pp. 613-619.
Study of Treatment Variation in the Radiotherapy of Head and Neck Tumors Using a Fiber-Optic On-Line Radiotherapy Imaging System, Halverson K. et al., 1991, pp. 1327-1336.
Bortfeld et al., "Clinically relevant intensity modulation optimization using physical criteria," In Proceedings of the XII International Conference on the Use of Computers in Radiation Therapy, Salt Lake City, Utah, 1-4 (1997).
Yan, D. et al., "Computed tomography guided management of interfractional patient variation", Semin. Radiat, Oncol. 15, 168-179 (2005).
Court, L. et al, "An automatic CT-guided adaptive radiation therapy technique by on-line modification of MLC leaf positions for prostate cancer", Int. J. Radiat. Oncol., Biol., Phys. 62(1), 154-163 (2005).
Mohan, R. et al., "Use of deformed intensity distributions for on-line modification of image-guided IMRT to account for interfractional anatomic changes", Int. J. Radiat. Oncol., Biol., Phys. 61(4), 1258-1266 (2005).
MacKie, T.R. et al., "Image guidance for precise conformal radiotherapy", Int. J. Radiat. Oncol., Biol., Phys. 56(1), 89-105 (2003).
Brock, K.K. et al., "Feasibility of a novel deformable image registration technique to facilitate classification, targeting, and monitoring of tumor and normal tissue", Int. J. Radiat. Oncol., Biol., Phys. 64(4), 1245-1254 (2006).
Davis, B.C. et al., "Automatic segmentation of intra-treatment CT images for adaptive radiation therapy of the prostate", Med. Image Comput. Comput. Assist. Interv. Int. Conf. Med. Image. Comput. Comput. Assist Interv. 8(Pt 1), 442-450 (2005).
Foskey, M., "Large deformation three-dimensional image registration in image-guided radiation therapy", Phys. Med. Biol. 50(24), 5869-5892 (Dec. 7, 2005).
Munbodh, R. et al., "Automated 2D-3D registration of a radiograph and a cone beam CT using line-segment enhancement", Med. Phys. 33(5), 1398-1411 (Apr. 27, 2006).
Court, L.E. et al., "Automatic online adaptive radiation therapy techniques for targets with significant shape change: A feasibility study", Phys. Med. Biol. 51(10), 2493-2501 (Apr. 27, 2006).
Godfrey, D.J. et al., "Digital tomosynthesis with an on-board kilovoltage imaging device", Int. J. Radiat. Oncol., Biol., Phys. 65(1), 8-15 (2006).
Mestovic, A. et al., "Direct aperture optimization for online adaptive radiation therapy", Med. Phys. 34(5), Apr. 19, 2007, pp. 1631-1646.
Cortrutz, C. et al., "Segment-based dose optimization using a genetic algorithm", Phys. Med. Biol. 48(18), 2987-2998 (2003).
Bedford, J.L. et al., "Constrained segment shapes in direct-aperture optimization for step-and shoot IMRT", Med. Phys. 33(4). 944-958 (Mar. 17, 2006).
Kirkpatrick, S. et al., "Optimization by simulated annealing", Science 220, 671-680 (1983).
I.M.R.T.C.W. Group, "Intensity-modulated radiotherapy: Current status and issues of interest", Int. J. Radiat. Oncol., Biol., Phys. 51(4), 880-914 (2001).
Niemierko, A. et al., "Random sampling for evaluation treatment plans", Med. Phys. 17(5), 753-762 (1990).
Chui, C.S. et al., "Dose calculation for photon beams with intensity modulation generated by dynamic jaw or multileaf collimations", Med. Phys, 21(8), 1237-1244 (1994).
Ghilezan, M.J. et al., "Prostate gland motion assessed with cine-magnetic resonance imaging (cine-MRI)", Int. J. Radiat. Oncol., Biol., Phys. 62(2), 406-417 (2005).
Nichol, A.M. et al., "Intra-prostatic fiducial markers and concurrent androgen deprivation", Clin. Oncol. (R Coll. Radiol) 17(6), 465-468 (2005).
Zellars, R.C. et al., "Prostate position late in the course of external beam therapy: Patterns and predictors", Int. J. Radiat. Oncol., Biol., Phys. 47(3), 655-660 (2000).
Sanguineti, G. et al., "Neoadjuvant androgen deprivation and prostate gland shrinkage during conformal radiotherapy", Radiother, Oncol. 66(2), 151-157 (2003).
Nichol, A.M. et al., "A magnetic resonance imaging study of prostate deformation relative to implanted gold fiducial markers", Int. J. Radiat. Oncol., Biol., Phys. 67(1), 48-56 (2007).
R.T.O.G. 0415, "A Phase III Randomized Study of Hypofractionated 3D-CRT/IMRT Versus Conventionally Fractionated 3D-CRT/IMRT in patients with favourable-risk prostate cancer", (www.RTOG.orgaccessed on Jul. 2006) (2006).
Yan, D. et al., "The influence of interpatient and intrapatient rectum variation on external beam treatment of prostate cancer", Int. J. Radiat. Oncol., Biol., Phys. 51(4), 1111-1119 (2001).
Hoogeman, M.S. et al, "A model to simulate day-to-day variations in rectum shape", Int. J. Radiat. Oncol., Biol., Phys. 54(2), 615-625 (2002).
Jiang, Z. et al., "An examination of the number of required apertures for step-and-shoot-IMRT", Phys. Med. Biol. 50 (23), 5653-5663 (Nov. 24, 2005).
Earl et al., "Inverse Planning for Intensity-Modulated Arc Therapy Using Direct Aperture Optimization", Physics in Medicine and Biology 48 (2003), Institute of Physics Publishing, pp. 1075-1089.
Spirou et al., "A Gradient Inverse Planning Algorithm with Dose-Volume Contraints", Med. Phys. 25, pp. 321-333 (1998).
Wu et al., "Algorithm and Functionality of an Intensity Modulated Radiotherapy Optimization System", Med. Phys. 27, pp. 701-711 (2000).
Spirou et al., "Generation of Arbitrary Intensity Profiles by Dynamic Jaws or Multileaf Collimators", Med. Phys. 21, pp. 1031-1041 (1994).
Xia et al., "Multileaf Collimator Leaf Sequencing Algorithm for Intensity Modulated Beams with Multiple Static Segments", Med. Phys. 25, pp. 1424-1434 (1998).
Otto et al., "Enhancement of IMRT Delivery through MLC Rotation", Phys. Med. Biol. 47, 3997-4017 (2002).
Shepard et al., "Direct Aperture Optimization: A Turnkey Solution for Step-and-Shoot IMRT", Med. Phys. 29 (6) (2002), pp. 1007-1018.
Tervo et al., "A Model for the Control of a Multileaf Collimator in Radiation Therapy Treatment Planning", Inverse Problems 16 (2000), pp. 1875-1895.

(56) References Cited

OTHER PUBLICATIONS

Shepard et al., "An Arc-Sequencing Algorithm for Intensity Modulated Arc Therapy", Med. Phys. 34 (2) (2007), pp. 464-470.
Cao et al., "Continuous Intensity Map Optimization (CIMO): A Novel Approach to Leaf Sequencing in Step and Shoot IMRT", Med. Phys. 33 (4) (2006), pp. 859-867.
Ulrich et al., "Development of an Optimization Concept for Arc-Modulated Cone Beam Therapy", Phys. Med. Biol. 52 (2007), pp. 4099-4119.
Hardemark et al., "Direct Machine Parameter Optimization with RayMachine in Pinnacle", RaySearch White Paper, RaySearch Laboratories (2003), pp. 1-3.
C. X. Yu, "Intensity-modulated arc therapy with dynamic multileaf collimation: An alternative to tomotherapy," Phys. Med. Biol. 40, pp. 1435-1449, 1995.
Gladwish, A. et al., "Segmentation and leaf sequencing for intensity modulated arc therapy," Med. Phys. 34, pp. 1779-1788, 2007.
Wong, E. et al., "Intensity-modulated arc therapy simplified," Int. J. Radiat. Oncol. Biol. Phys. 53, pp. 222-235, 2002.
Bratengeier, K. "2-Step IMAT and 2-Step IMRT in three dimensions," Med. Phys. 32, pp. 3849-3861, 2005.
Cameron, C., "Sweeping-window arc therapy: An implementation of rotational IMRT with automatic beam-weight calculation," Phys. Med. Biol. 50, pp. 4317-4336, 2005.
Crooks, S.M. et al., "Aperture modulated arc therapy," Phys. Med. Biol. 48, pp. 1333-1344, 2003.
De Gersem, W. et al. "Leaf position optimization for step-and-shoot IMRT," Int. J. Radiat. Oncol. Biol. Phys. 51, pp. 1371-1388, 2001.
Milette, M.P. et al., "Maximizing the potential of direct aperture optimization through collimator rotation," Med. Phys. 34, pp. 1431-1438, 2007.
R. A. Reynolds, M. R. Sontag, and L. S. Chen, "An algorithm for three-dimensional visualization of radiation therapy beams", Med. Phys. 15, pp. 24-28, 1988.
Ning, R, Wang, X., Shen, J, Conover DL., An Image Intensifier-Based Volume Tomograpric Angiography Imaging System: System Evaluation, SPIE, 2432 280-290.
Uematsu, M., Fukui, T., Shioda, A., Tokumitsu, H., Takai, K., Kojima, T., Asai, Y. Kusano, S., Dual Computed Tomography Linear Accelerator Unit for Stereotactic Radiation Therapy: A New Approach Without Cranially Fixated Stereotactic Frames, Int. J. Radiation Oncology Biol. Phys., vol. 35, No. 3, pp. 587-592, 1996.
Varian 2002 Annual Report, 2002, p. 1-28.
Ferris, M. et al., "An Optimization Approach for Radiosurgery Treatment Planning", 2003, p. 921-937.
Ferris, M. et al., "Radiosurgery Treatment Planning via Nonlinear Programming", 2003, p. 247-260.
Rowbottom, C. et al., "Simultaneous optimization of beam orientations and beam weights in conformal radiotherapy", 2001, p. 1696-1702.
Scholz, C. et al., "Development and clinical application of a fast superposition algorithm in radiation therapy", 2003, p. 79-90.
Simo Muinonen, "Sadehoiden valmistelun optimointi fysiikan keinoin", 1995, p. 1-166.
Pekka Kolmonen, "The direct control of the Multi-Leaf Collimator in the inverse problem of radiotherapy treatment planning", Mar. 19, 2004, p. 1-81.
Jyrki Alakuijala, "Algorithms for modeling anatomic and target volumes in image-guided neurosurgery and radiotherapy", 2001, p. 1-121.
Heikki Joensuu, "Intensiteettimuokattu sadehoito—uusi tekniikka parantanee hoitotuloksia", 2001, p. 389-394.
Tina Seppala, "FiR 1 epithermal neutron beam model and dose calculation for treatment planning in neutron capture therapy", 2002, p. 1-46.
Smith, R. et al., "Development of cone beam CT for radiotherapy treatment planning", 2001, p. 115.
Arnfield et al., "The use of film dosimetry of the penumbra region to improve the accuracy of intensity modulated radiotherapy", 2005, p. 12-18.
Bergman et al., "The use modified single pencil beam dose kernels to improve IMRT dose calculation accuracy", 2004, p. 3279-3287.
Budgell, "Temporal resolution requirements for intensity modulated radiation therapy delivered by multileaf collimators", 1999, p. 1581-1596.
Xing et al., "Dosimetric verification of a commercial inverse treatment planning system", 1999, p. 463-478.
Preciado-Walters, "A coupled column generation, mixed integer approach to optimal planning of intensity modulated radiation therapy for cancer", 2004, p. 319-338.
Sidhu, K. et al., "Optimization of Conformal Thoracic Radiotherapy Plance While Using Cone-Beam CT Imaging for Treatment Verification", 2001, p. 175-176.
Xing et al., "Iterative methods for inverse treatment planning", 1996, p. 2107-2123.
Malik, R. et al., "Simulator Based CT: 4 Years of Experience at the Royal North Shore Hospital", Sydney, Australia, 1993, p. 177-185.
Webb et al., "Inverse planning with constraints to generate smoothed intensity-modulated beams", 1998, p. 2785-2794.
Crooks et al., "Linear algebraic methods applied to intensity modulated radiation therapy", 2001, p. 2587-2606.
Varian Medical Systems, Radiation Therapy Acuity, 2005, 1 page.
Anderson, R., "Software system for automatic parameter logging on Philips SL20 linear accelerator", 1995, p. 220-222.
Jaffray, et al., "Cone-beam computed tomography on a medical linear accelerator using a flat-panel imager", 2000, p. 558-560.
Karzmark, C. J., "A Primer on Theory and Operation of Linear Accelerators in Radiation Therapy", 1981, p. 1-61.
Wong, J. et al., "Behandlung des Lungenkarzinoms mittels stereotaktischer Strahlentherapie unter Verwednung des weltweit ersten PRIMATOM Systems—eine Fallstudie", 2001, p. 133-136.
Kolda et al., "Optimization by Direct Search: New Perspectives on Some Classical and Modern Methods", 2003, p. 385-482.
Studholme et al., "Automated three-dimensional registration of magnetic resonance and positron emission tomography brain images by multiresolution optimization of voxel similarity measures", 1997, p. 25-35.
Lu et al., "Fast free-form deformable registration via calculus of variations", 2004, p. 3067-3087.
C.T. Kelly, "Iterative Methods for Optimization", North Carolina State University, Society for Industrial and Applied Mathematics, 1999, p. 1-188.
Dadone et al., "Progressive Optimization", Computers & Fluids, 29 (2000), p. 1-32.
R. Fletcher, "Practical Methods of Optimization", Department of Mathematics and Computer Science, University of Dundee, Scotland, UK, Wiley-Interscience Publication,1987, p. 1-436.
Singiresu S. Rao, "Engineering Optimization: Theory and Practice", 1996, p. 1-840.
Rangarajan K. Sundaram, "A First Course in Optimization Theory", New York University, Cambridge University Press, 1996.
Christos H. Papadimitriou, "Combinatorial Optimization: Algorithms and Complexity", Dover Books on Mathematics, 1982, Chapter 1, p. 2-25.
Jan Blachut et al., "Emerging Methods for Multidisciplinary Optimization", CISM Courses and Lectures No. 425, International Centre for Mechanical Science, 2001, p. 1-337.
Powell, M.J.D., "Direct search algorithms for optimization calculations", Cambridge University Press, Acta Numerica (1998), p. 287-336.
Rostkowska, J. et al., "Physical and Dosimetric Aspects of Quality Assurance in Sterotactic Radiotherapy", 2001, p. 53-54.
Munro, P., "On Line Portal Imaging", 1997, p. 114.
Maria Korteila, "Varianin avulla Ade tappaa kasvaimen tarkasti", 2000, p. 1-8.
Sharpe M. et al., Monitor unit settings for intensity modulated beams delivered using a step-and-shoot approach, 2000, pp. 2719-2725.
Shiu A. et al., Verification data for electron beam dose algorithms, 1992, pp. 623-636.
Michalski J. et al., The Use of On-line Image Verification to Estimate the Variation in Radiation Therapy Dose Delivery, 1993, pp. 707-716.

(56) References Cited

OTHER PUBLICATIONS

Siewerdsen J. et al., Signal, noise power spectrum, and detective quantum efficiency of indirect-detection flat-panel imagers for diagnostic radiology, 1998, pp. 614-628.
Sharpe M. et al., Compensation of x-ray beam penumbra in conformal radiotherapy, 2000, pp. 1739-1745.
Purdy J. et al., State of the Art of High Energy Photon Treatment Planning,1987, pp. 4-24.
Michalski J. et al., Prospective Clinical Evaluation of an Electronic Portal Imaging Device, 1996, pp. 943-951.
Oldham M. et al., Practical aspects of in situ 16O (y,n) 15O activation using a conventional medical accelerator for the purpose of perfusion imaging, 2001, pp. 1669-1678.
Mohan R., Three-Dimensional Dose Calculations for Radiation Treatment Planning, 1991, pp. 25-36.
Milliken B. et al., Verification of the omni wedge technique, 1998, pp. 1419-1423.
P. Rizo, P. Grangeat, P. Sire, P. Lemasson, and P. Melennec, Comparison of two three-dimensional x-ray cone-beam-reconstruction algorithms with circular source trajectories, J. Opt. Soc. Am. A 8: 1639-1648. 1991.
Swindell, W., Simpson, R.G., Oleson, J.R., Chen, C.T., Grubbs, E.A., Computed tomography with a linear accelerator with radiotherapy applications, Medical Physics 10, 416-420, 1983.
Siewerdsen, JH and Jaffray, D.A. Cone-beam computed tomography with a flat-panel imager: Magnitude and effects of xray scatter, Medical Physics 28: 220-231, 2001.
Ragan, D.P., Tongming He, T., Liu, X., Correction for distortion in a beam outline transfer device in radiotherapy CT-based simulation, Medical Physics 20: 179-185 ,1993.
Uematsua, M., Sonderegger, M., Shioda, A., Taharaa, K., Fukui, T., Hama, Y., Kojima, T., Wong, J.R., Kusanoa, S., Daily positioning accuracy of frameless stereotactic radiation therapy with a fusion of computed tomography and linear accelerator (focal) unit: evaluation of z-axis with a z-marker, Radiotherapy and Oncology 50: 337-339, 1999.
Yan, X. H., and Leahy, R.M., Derivation and Analysis of a Filtered Backprojection Algorithm for Cone Beam Projection Data, IEEE Transactions on Medical Imaging. 10, 462-472, 1991.
Ning, R., Chen, B., Yu, R., Conover, D. Tang, X., Ning, Y., Flat Panel Detector-Based Cone-Beam Volume CT Angiography Imaging: System Evaluation, IEEE Transactions on Medical Imaging, 19: 949-963, 2000.
Uematsua, M., Shioda, A., Suda, A., Taharaa, K., Kojima, T, Hama, Y, Kono, M., Wong, J.R., Fukui, T, Kusanoa, S., Intrafractional Tumor Position Stability During Computed Tomography (CT)-Guided Frameless Stereotactic Radiation Therapy for Lung or Liver Cancers With a Fusion of CT and Linear Accelerator (Focal) Unit, Int. J. Radiation Oncology Biol. Phys., 48: 443-448, 2000.
Kestin L. et al., Intensity Modulation to Improve Dose Uniformity With Tangential Breast Radiotherapy: Initial Clinical Experience, 2000, pp. 1559-1568.
Jaffray D. et al., Conebeam Tomographic Guidance of Radiation Field Placement for Radiotherapy of the Prostate, 1998, pp. 1-32.
Jaffray D. et al., Dual-Beam Imaging for Online Verification of Radiotherapy Field Placement,1995, pp. 1273-1280.
Jaffray D. and Wong J., Exploring "Target of the Day" Strategies for a Medical Linear Accelerator With Conebeam-CT Scanning Capability,1997, pp. 172-174.
Jaffray D. and Wong J., Managing Geometric Uncertainty in Conformal Intensity-Modulated Radiation Therapy, 1999, pp. 4-19.
Jaffray D., X-ray scatter in megavoltage transmission radiography: Physical characteristics and influence on image quality, 1994, pp. 45-60.
Jaffray D. and Battista J., X-ray sources of medical linear accelerators: Focal and extra-focal radiation, 1993, pp. 1417-1427.
Herman M. et al., Clinical use of electronic portal imaging: Report of AAPM Radiation Therapy Committee Task Group 58, 2001, pp. 712-737.
Harms W. et al., A software tool for the qualitative evaluation of 3D dose calculation algorithms,1998, pp. 1830-1836.
Michalski J. et al., An Evaluation of Two Methods of Anatomical Alignment of Radiotherapy Portal Images, 1993, pp. 1199-1206.
Laughlin J. et al. Evaluation of High Energy Photon External Beam Treatment Planning: Project Summary, 1991, pp. 3-8.
Martinez A. et al., Improvement in Dose Escalation Using the Process of Adaptive Radiotherapy Combined with Three-Dimensional Conformal or Intensity-Modulated Beams for Prostate Cancer, 2001, pp. 1226-1234.
Masterson M. et al., Interinstitutional Experience in Verification of External Photon Dose Calculations,1991, pp. 37-58.
Kini V. et al., Use of Three-Dimensional Radiation Therapy Planning Tools and Intraoperative Ultrasound to Evaluate High Dose Rate Prostate Brachytherapy Implants., 1999, pp. 571-578.
Stromberg, J.S., Sharpe, M.D., Kim, L.H., Kini, V.R., Jaffray, D.A., Martinez, A.A., Wong, J.W., Active Breathing control (ABC) for Hodgkins Disease Reduction in Normal Tissue Irradiation with Deep Inspiration and Implications for Treatment, Int. J. Radiation Oncology Biol. Phys.,2000 vol. 48, pp. 797-806.
Siewerdsen J. et al., Empirical and theoretical investigation of the noise performance of indirect detection, active matrix flat-panel imagers (AMFPIs) for diagnostic radiology, 1997, pp. 71-89.
Perera H. et al., Rapid Two-Dimensional Dose Measurement in Brachytherapy Using Plastic Scintillator Sheet: Linearity, Signal-to-Noise Ratio, and Energy Response Characteristics, 1992, pp. 1059-1069.
Jaffray D. et al., Activity distribution of a cobalt-60 teletherapy source, 1991, pp. 288-291.
Kestin L. et al., Improving the Dosimetric Coverage of Interstitial High-Dose-Rate Breast Implants, 2000, pp. 35-43.
Boyer et al., A review of electronic portal imaging devices (EPIDs), 1992, pp. 1-16.
Development of a Second-Generation Fiber-Optic On-Line Image Verification System, Wong J. et al., 1993, pp. 311-320.
Effect of small Inhomogeneities on dose in a cobalt-60 beam, Wong J. et al., 1981, pp. 783-791.
On methods of inhomogeneity corrections for photon transport, Wong J. and Purdy J., 1990, pp. 807-814.
A new approach to CT pixel-based photon dose calculations in heterogeneous media, Wong J. and Henkelman M., 1983, pp. 199-208.
On-line image verification in radiation therapy: an early USA experience, Wong J. et al., 1993, pp. 43-54.
On-line Readiotherapy Imaging with an Array of Fiber-Optic Image Reducers, Wong J. et al., 1990, pp. 1477-1484.
Portal Dose Images I: Quantitative Treatment Plan Verification, Wong J. et al., 1990, pp. 1455-1463.
Reconsideration of the power-law (Batho) equation for inhomogeneity corrections, Wong J. and Henkelman M., 1982, pp. 521-530.
Role of Inhomogeneity Corrections in Three-Dimensional Photon Treatment Planning, Wong J. et al., 1991, pp. 59-69.
Second scatter contribution to dose in a cobalt-60 beam, Wong J. et al., 1981, pp. 775-782.
Treatment Verifications and Patient Dose Estimations Using Portal Dose Imaging, Wong J. et al., 1988, pp. 213-225.
The Use of Active Breathing Control (ABC) to Reduce Margin for Breathing Motion, Wong J. et al., 1999, pp. 911-919.
Implementing multiple static field delivery for intensity modulated beams, Wu Y. et al., Nov. 2001, pp. 2188-2197.
The Use of Adaptive Radiation Therapy to Reduce Setup Error: A Prospective Clinical Study, Yan D. et al., 1998, pp. 715-720.
Adaptive Radiation Therapy, Yan D. et al., 1997, pp. 123-132.
The Influence of Interpatient and Intrapatient Rectum Variation on External Beam Treatment of Prostate Cancer, Yan D. et al., 2001, pp. 1111-1119.
A Model to Accumulate Fractionated Dose in a Deforming Organ, Yan D. et al., 1999, pp. 665-675.
A New Model for "Accept or Reject" Strategies in Off-Line and On-Line Megavoltage Treatment Evaluation, Yan D. et al., 1995, pp. 943-952.

(56) References Cited

OTHER PUBLICATIONS

Portal Dose Images II: Patient Dose Estimation, Ying X. et al., 1990, pp. 1465-1475.
A method for implementing dynamic photon beam intensity modulation using independent jaws and a multileaf collimator, Yu C. et al., 1995, pp. 769-787.
A multiray model for calculating electron pencil beam distribution, Yu C. et al., 1988, pp. 662-671.
Photon dose perturbations due to small inhomogeneities, Yu C. et al., 1987, pp. 78-83.
Photon does calculation incorporating explicit electron transport, Yu C. et al., Jul. 1995, pp. 1157-1166.
Optimization of the scintillation detector in a combined 3D megavoltage CT scanner and portal imager, Mosleh-Shirazi M. et al., Oct. 1998, pp. 1880-1890.
Advanced Workstation for Irregular Field Simulation and Image Matching, MDS Nordion, 1999, 7 pages.
A video-Based Patient Contour Acquisition System for the Design Radiotherapy Compensators, Andrew, et al., 1989, pp. 425-430.
Daily Targeting of Intrahepatic Tumors for Radiotherapy, Baiter, James M. et al., 2002, pp. 266-271.
Automatic generation of beam apertures, Brewster, et al., 1993, pp. 1337-1342.
Intensity-modulated arc therapy with dynamic multileaf collimation: An alternative to tomotherapy, C. X. Yu, 1995, pp. 1435-1449.
Cone-Beam CT for Radiotherapy Applications, Cho, Paul S. et al., 1995, pp. 1863-1883.
Characterization of a Fluoroscopic Imaging System for kV and MV Radiography, Drake, D.G. et al., May 2000, pp. 898-905.
Inverse Planning for Intensity-Modulated Arc Therapy Using Direct Aperture Optimization, Earl et al., 2003, pp. 1075-1089.
Interactive image segmentation for radiation treatment planning, Elliott, PJ, et al., 1992, pp. 620-634.
Three-Dimensional Computed Tomographic Reconstruction Using a C-Arm Mounted XRII: Image Based Correction of Gantry Motion Nonidealities, Fahrig and Holdsworth, Jan. 2000, pp. 30-38.
Practical Cone-Beam Algorithm, Feldkamp, L.A. et al., Jun. 1984, pp. 612-619.
Three-dimensional radiation planning. Studies on clinical integration, Gademann, G, et al., 1993, pp. 159-167.
A Performance Comparison of Flat-Panel Imager-Based MV and kV Conebeam CT, Groh, B A., et al., Jun. 2002, pp. 967-975.
A ghost story: spatio-temporal response characteristics of an indirect-detection flat- panel imager, J. H. Siewerdsen and D. A. Jaffray, 1999, pp. 1624-1641.
Flat-Panel Cone-Beam Computed Tomography for Image-Guided Radiation Therapy, Jaffray et al., 2002, pp. 1337-1349.
A Radiographic and Tomographic Imaging System Integrated into a Medical Linear Accelerator for Localization of Bone and Soft-Tissue Targets, Jaffray, D A., et al., 1999, pp. 773-789.
Cone-beam CT: applications in image-guided external beam radiotherapy and brachytherapy, Jaffray, DA, et al., Jul. 2000, p. 2044.
A CCTV-Microcomputer Biostereometric System for Use in Radiation Therapy (Topography, Medical Physics, Tissue Compensators) Optimization by simulated annealing, Keys, D , et al., 1984, p. 3857.
Feasible Cone Beam Scanning Methods for Exact Reconstruction in Three-Dimensional Tomography, Kudo et al., 1990, p. 2169.
AIM Project A2003: COmputer Vision in RAdiology (COVIRA), Kuhn, MH, Oct. 1994, pp. 17-31.
New development of integrated CT simulation system for radiation therapy planning, Kushima, T, et al., 1993, pp. 197-213.
Patient Beam Positioning System Using CT Images, Masshiro, et al., 1982, pp. 301-305.
A Feasibility Study for Megavoltage Cone Beam CT Using a Commercial EPID, Midgley, S., et al., 1998, pp. 155-169.
Intersection of shaped radiation beams with arbitrary image sections, Mohan, R, et al., Jun. 1987, pp. 161-168.
Active Breathing Control (ABC) for Hodgkin's Disease: Reduction in Normal Tissue Irradiation with Deep Inspiration and Implications for Treatment, Stromberg J. et al., 2000, pp. 797-806.
State-of-the-Art of External Photon Beam Radiation Treatment Planning, Sontag M. et al., 1991, pp. 9-23.
Ruchala, K.J., Olivera, G.H., Schloesser, E.A., Mackie, T.R., Megavoltage CT on a tomotherapy system, Phys. Med. Biol. 44: 2597-2621, 1999.
Siewerdsen, J.H. and Jaffray, D.A., Optimization of x-ray imaging geometry (with specific application to flat-panel conebeam computed tomography), Medical Physics 27: 1903-1914, 2000.
Redpath, A.T., Wright, D.H., The use of a Simulator and Treatment Planning Computer as a CT Scanner for Radiotherapy Planning, Eight International Conference on the use of computer in radiation therapy, IEEE Computer Society Press, ISBN 0-8186-0559-6, 1984.
Pisani, L., Lockman, D., Jaffray, D.,Yan, D. Martinez, A., Wong, J., Setup Error in Radiotherapy: On-Line correction Using Electronic Kilovoltage and Megavoltage Radiographs.
Analysis of various beamlet sizes for IMRT with 6 MV Photons, Sohn et al., 2003, pp. 2432-2439.
Guidance document on delivery, treatment planning, and clinical implementation of IMRT: Report of the IMRT subcommittee of the AAPM radiation therapy committee, Ezzell et al., Aug. 2003, pp. 2089-2115.
The Relationship Between the Number of Shots and the Quality of Gamma Knife Radiosurgeries, Cheek et al., 2005, pp. 449-462.
Automatic Variation of Field Size and Dose Rate in Rotation Therapy, Mantel and Perry, 1977, pp. 697-704.
The Physics of Intensity-Modulated Radiation Therapy, Boyer, 2002, pp. 38-44.
Sampling Issues for Optimization in Radiotherapy, Ferris et al., 2006, pp. 95-115.
Comparison of CT numbers determined by a simulator CT & a diagnostic scanner, M. Hartson, D. Champney, J. Currier, J. Krise, J. Marvel, M. Schrijvershof, J. Sensing, 1995, pp. 37-45.
The application of dynamic field shaping and dynamic does rate control in conformal rotational treatment of prostate, Tobler, 2003.
Optimization of Gamma Knife Radiosurgery, Ferris et al., Apr. 8, 2004, pp. 1-76.
Nakagawa, Keiichi, et al., Megavoltage CT-Assisted Stereotactic Radiosurgery for Thoracic Tumors: Original Research in the Treatment of Thoracic Neoplasms, 2000, pp. 449-457.
AAPM Report No. 54—Stereotactic Radiosurgery, Schell et al., Jun. 1995, pp. 1-88.
Mueller, Fast and Accurate Three-Dimensional Reconstruction from Cone-Beam Projection Data Using Algebraic Methods,1998, pp. 1-114.
Effects of the intensity levels and beam map resolutions on static IMRT plans, Sun et al., 2004, pp. 2402-2411.
Hatano, Clinical application of IMRT, 2002, pp. 199-204.
Ferris et al., An optimization approach for radiosurgery treatment planning, 2003, vol. 13, pp. 921-937.
Selected pages of Appendix 2 to Complainants' Eighth Supplemental Responses and Objections to Respondents' First Set of Interrogatories, dated Mar. 28, 2016 in Certain Radiotherapy Systems and Treatment Planning Software, and Components Thereof, Investigation No. 337-TA-968.
S. Agostinelli, F. Foppiano, A prototype 3D CT extension for radiotherapy simulators, 2001, pp. 11-21.
A cone-beam megavoltage CT scanner for treatment verification in conformal radiotherapy, M. Shirazi, P. Evans, W. Swindell, S. Webb, M. Partridge, 1998, pp. 319-328.
Comparison of flat-panel detector and image-intensifier detector for cone-beam CT, R. Baba, Y. Konno, K. Ueda, S. Ikeda, 2002, pp. 153-158.
Partridge et al., Linear accelerator output variations and their consequences for megavoltage imaging, 1998, pp. 1443-1452.
Novel Approximate Approach for High-Quality Image Reconstruction in Helical Cone Beam CT at Arbitrary Pitch, Schaller et al., 2001, pp. 113-127.
Digital radiotherapy simulator, P. Cho, K. Lindsley, J. Douglas, K. Stelzer, T. Griffin, 1998, pp. 1-7.
Signal, noise, and readout considerations in the development of amorphous silicon photodiode arrays for radiotherapy and diagnostic x-ray imaging, Antonuk et al., 1991, pp. 108-119.

(56) References Cited

OTHER PUBLICATIONS

Electronic portal imaging devices: a review and historical perspective of contemporary technologies and research, Antonuk, 2002, pp. R31-R65.
Mosleh-Shirazi et al., Rapid portal imaging with a high-efficiency, large field-of-view detector, 1998, pp. 2333-2346.
Vicini F. et al., Low-Dose-Rate Brachytherapy as the Sole Radiation Modality in the Management of Patients with Early-Stage Breast Cancer Treated with Breast-Conserving Therapy: Preliminary Results of a Pilot Trial, 1997, pp. 301-310.
Williamson J. et al., One-dimensional scatter-subtraction method for brachytherapy dose calculation near bounded heterogeneities, 1993, pp. 233-244.
Wong J. et al., Conservative management of osteoradionecrosis, 1997, pp. 16-21.
Wong J. et al., The Cumulative Verification Image Analysis Tool for Offline Evaluation of Portal Images, 1995, pp. 1301-1310.
Vicini F. et al., Implementation of 3D-Virtual Brachytherapy in the Management of Breast Cancer: A Description of a New Method of Interstitial Brachytherapy, 1998, pp. 620-635.
Teicher B. et al., Allosteric effectors of hemoglobin as modulators of chemotherapy and radiation therapy in vitro and in vivo,1998, pp. 24-30.
Tepper J. et al., Three-Dimensional Display in Planning Radiation Therapy: A Clinical Perspective, 1991, pp. 79-89.
Urie M. et al., The Role of Uncertainty Analysis in Treatment Planning, 1991, pp. 91-107.
Vicini F. et al., Dose-Volume Analysis for Quality Assurance of Interstitial Brachytherapy for Breast Cancer,1999, pp. 803-810.
Verfaillie G, Lemaitre M, Schiex T. Russian Doll Search for Solving Constraint Optimization Problems. 1996. AAAI-96 Proceedings: 181-187.
Wang X, Zhang X, Dong L, Liu H, Wu Q, Mohan R.. Development of methods for beam angle optimization for IMRT using an accelerated exhaustive search strategy. Int J Radiat Oncol Biol Phys. 2004. 60(4):1325-37.
Low DA, Mutic S, Dempsey JF, Markman J, Goddu SM, Purdy JA. Abutment region dosimetry for serial tomotherapy. Int J Radiat Oncol Biol Phys. 1999. 45(1):193-203.
Meedt G, Alber M, Nüsslin F.. Non-coplanar beam direction optimization for intensity-modulated radiotherapy. Phys Med Biol. 2003. 48(18):2999-3019.
Galvin JM, Chen XG, Smith RM. Combining multileaf fields to modulate fluence distributions. Int J Radiat Oncol Biol Phys. Oct. 20, 1993;27(3):697-705.
Mosleh-Shirazi MA, Evans PM, Swindell W, Webb S, Partridge M.. A cone-beam megavoltage CT scanner for treatment verification in conformal radiotherapy. Radiother Oncol. 1998. 48(3):319-28.
Podgorsak EB, Olivier A, Pla M, Lefebvre PY, Hazel J. Dynamic stereotactic radiosurgery. Int J Radial Oncol Biol Phys. 1988. 14(1):115-26.
Tobler M, Watson G, Leavitt DD. The application of dynamic field shaping and dynamic dose rate control in conformal rotational treatment of the prostate. Med Dosim. 2002 Winter;27(4):251-4.
Yu CX, Li XA, Ma L, Chen D, Naqvi S, Shepard D, Sarfaraz M, Holmes TW, Suntharalingam M, Mansfield CM. Clinical implementation of intensity-modulated arc therapy. Int J Radiat Oncol Biol Phys. 2002. 53(2):453-63.
Chin LM, Kijewski PK, Svensson GK, Bjärngard BE. Dose optimization with computer-controlled gantry rotation, collimator motion and dose-rate variation. Int J Radiat Oncol Biol Phys. 1983. 9(5):723-9.
Xia P, Chuang CF, Verhey LJ. Communication and sampling rate limitations in IMRT delivery with a dynamic multileaf collimator system. Med Phys. 2002. 29(3):412-23.
Duan J, Shen S, Fiveash JB, Brezovich IA, Popple RA, Pareek PN. Dosimetric effect of respiration-gated beam on IMRT delivery. Med Phys. 2003. 30(8):2241-52.
Bjamgard, BE, and Kijewski, PK. Computer-Controlled Radiation Therapy. Proceedings of the Annual Symposium on Computer Application in Medical Care. 1978 86-92.
Kumar MD, Thirumavalavan N, VenugopalKrishna D, Babaiah M. QA of intensity-modulated beams using dynamic MLC log files. 2006. Med. Phys., 31(1 ):36-41.
Gélinas D. Commissioning A Dynamic Multileaf Collimator On A Linear Accelerator. Thesis, Department of Medical Physics, McGill University, Montrea, Canada 1999.
Sillanpaa J, Chang J and Mageras G. Developments in megavoltage cone beam CT with an amorphous silicon EPID: Reduction of exposure and synchronization with respiratory gating 2005. Medical Physics, 32:819-829.
Takahashi S. Conformation Radiotherapy: Rotation Techniques As Applied to Radiography and Radiotherapy of Cancer, ACTA Radiologica Supplementum 242, Stockholm 1965. 11-142.
Duthoy W, De Gersem W, Vergote K, Coghe M, Boterberg T, De Deene Y, De Wagter C, Van Belle S, De Neve, W. Whole Abdominopelvic Radiotherapy (Waprt) Using Intensitymodulated Arc Therapy (Imat): First Clinical Experience Int. J. Radiation Oncology Biol, Phys,, 2003. 57:1019-1032.
Lof, J. Development of a general framework for optimization of radiation therapy. Department of Medical Radiation Physics, Stockholm 2000. pp. 1-42.
Clinac 600C & 600 C/D Equipment Specifications, Varian Medical Systems, 2000.
Clinac Accelerators, Varian Medical Systems, 2003.
Dynamic Beam Delivery (DBD) Toolbox User's Manual. Varian Medical Systems.
Chang SX, and Gibbons JP. Clinical Implementation of Non-Physical Wedges. AAPM Refresher Course presented at 41st Annual Meeting, American Association of Physicists in Medicine, Jul. 29, 1999.
Digital Imaging and Communications in Medicine (DICOM), Supplement 11, Radiotherapy Objects, final text dated Jun. 4, 1997, as a supplement to the DICOM Standard, and an extension to Parts 3, 4, and 6 of the published DICOM Standard.
DMLC Implementation Guide. ("DMLCIG"). Varian Medical Systems. 2006. 1-44.
Kaver G, Lind BK, Lof J, Liander A, Brahme A. Stochastic optimization of intensity modulated radiotherapy to account or uncertainties in patient sensitivity. Phys. Med. Biol. 1999. 44:2955-2969.
Lof J, Lind BK, Brahme A. Optimal radiation beam profiles considering the stochastic process of patient positioning in fractionated radiation therapy. Inverse Problems. 2005. 11:1189-1209.
Lof J, Lind BK, Brahme A. An adaptive control algorithm for optimization of intensity modulated radiotherapy considering uncertainties in beam profiles, patient set-up and internal organ motion. Phys. Med. Biol. 1998. 43:1605-1628.
Lof J, Lind BK, Liander A, Brahme A. Simultaneous Optimization of Beam Orientations and Intensity Modulation in Radiation Therapy Using the New Optimization Strategy P. ELEKTA-ITC968-00122743. pp. 1-18.

* cited by examiner

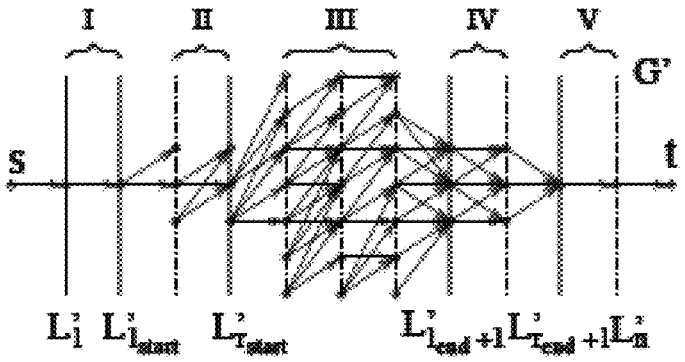
Fig. 2A
(Amended)
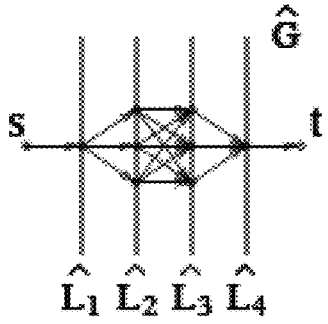
Fig. 2B
(Amended)
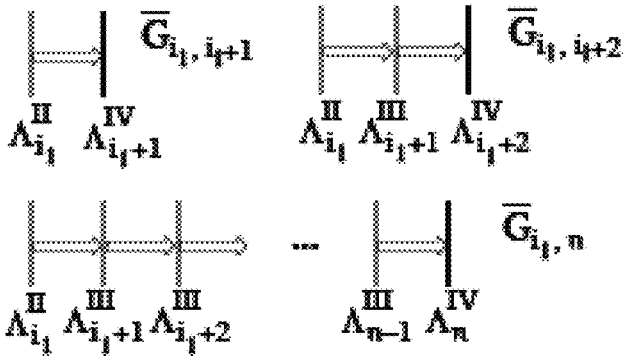
Fig. 2C
(Amended)
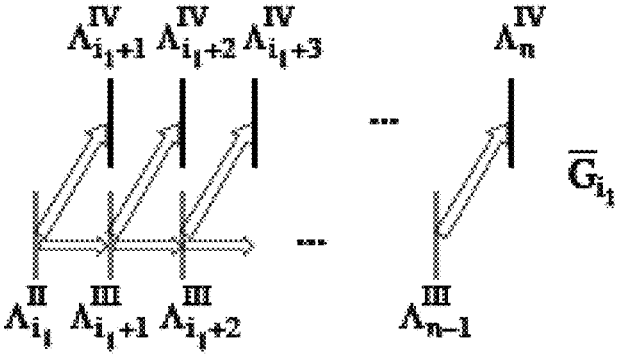
Fig. 2D
(Amended)

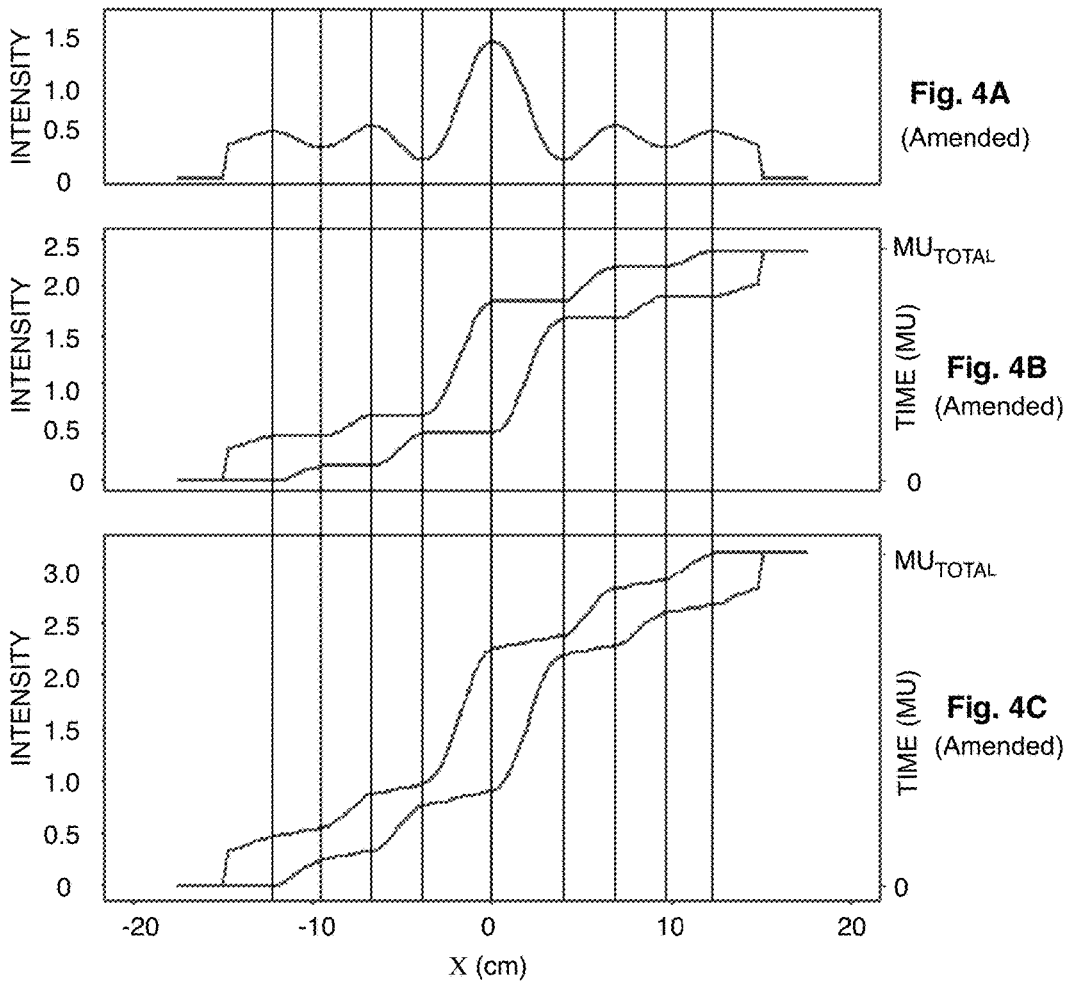
INTENSITY
1.5
1.0
0.5
0
Fig. 4A
(Amended)
INTENSITY
2.5
2.0
1.5
1.0
0.5
0
MU_TOTAL
TIME (MU)
0
Fig. 4B
(Amended)
INTENSITY
3.0
2.5
2.0
1.5
1.0
0.5
0
MU_TOTAL
TIME (MU)
0
Fig. 4C
(Amended)
-20
-10
0
10
20
X (cm)

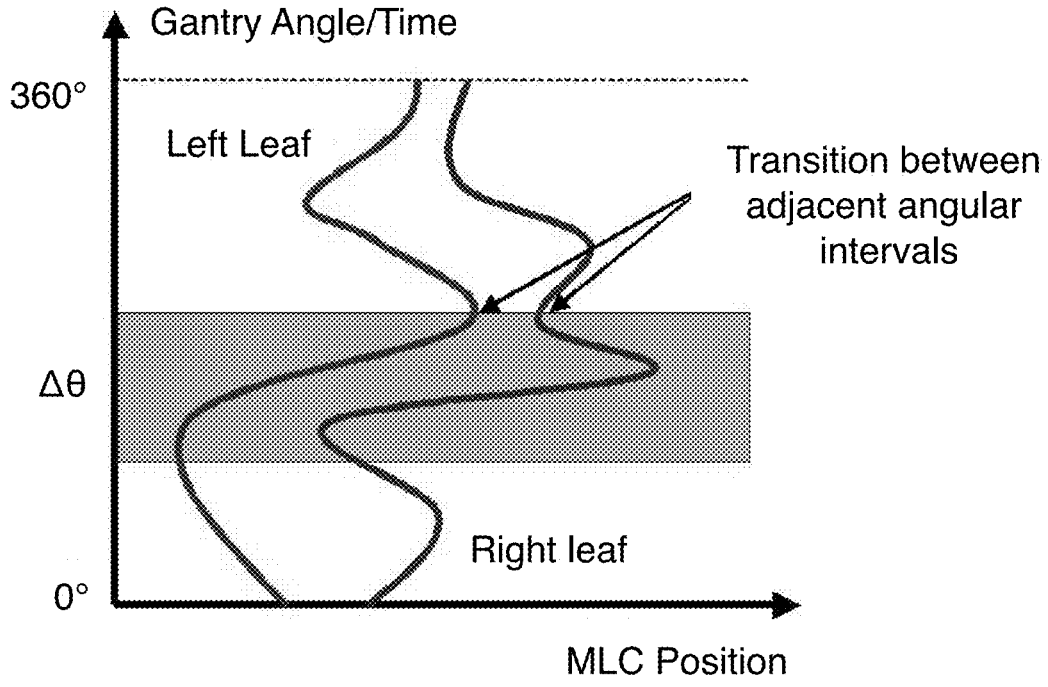
Fig. 7A
(Amended)
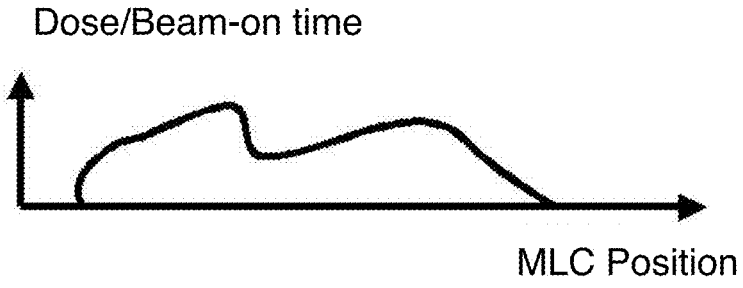
Fig. 7B
(Amended)

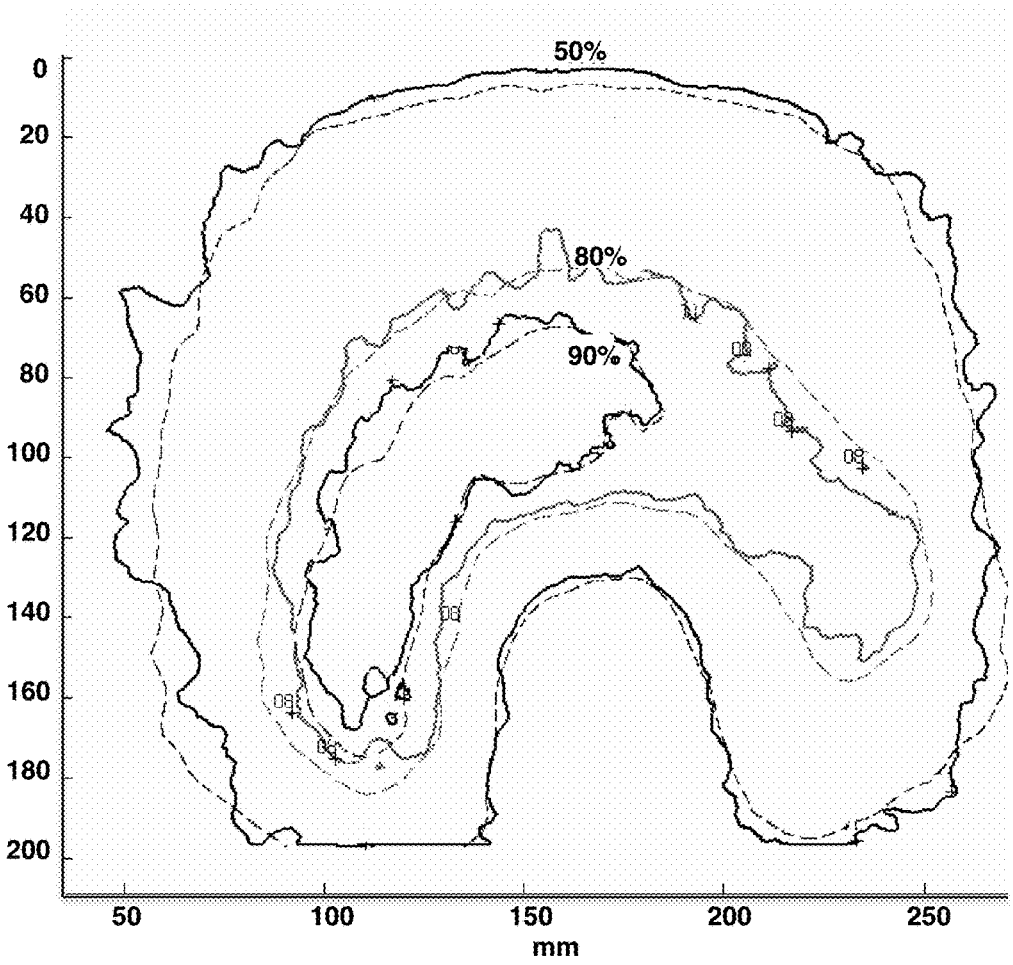
Fig. 10C
(Amended)

SINGLE-ARC DOSE PAINTING FOR PRECISION RADIATION THERAPY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FEDERAL FUNDING LEGEND

This work was supported by National Science Foundation Grant No. CCF-0515203 and by National Institutes of Health Grant No. CA117997. The U.S. Government has certain rights in this invention.

[CROSS-REFERENCE TO RELATED APPLICATIONS]

[This U.S. national application claims benefit of priority under 35 U.S.C. §120 of international application PCT/US2008/005028, filed Apr. 18, 2008 which claims benefit of priority under 35 U.S.C. § 119(e) of provisional application U.S. Ser. No. 61/913,175, filed Apr. 20, 2007, now abandoned.]

*CROSS-REFERENCE TO RELATED APPLICATIONS*

*This U.S. national application claims benefit of priority under 35 U.S.C. § 120 of international application PCT/US2008/005028, filed Apr. 18, 2008 which claims benefit of priority under 35 U.S.C. § 119(e) of provisional application U.S. Ser. No. 60/913,175, filed Apr. 20, 2007, now abandoned.*

BACKGROUND OF THE INVENTION

1. Field of the Invention

The present invention relates to the field of radiation oncology for malignant tumors and the like. Specifically, the present invention provides methods and systems for planning delivery of radiation therapy by means of a single-arc dose of radiation.

2. Description of the Related Art

Conformal radiation therapy is an important procedure available to the physician for the treatment of malignant tumors. Such therapy is used for eradicating or shrinking tumors that are relatively inaccessible to other modes of treatment such as surgical excision. However, because the ionizing radiation that is administered is damaging to both healthy and malignant tissue, it is important to confine the effect of the irradiation to the target tissue, to the extent possible, while sparing the adjacent tissue by minimizing irradiation thereto. To achieve this goal, various techniques of irradiating a target tumor with a defined beam of ionizing radiation have been devised.

Although simple masking techniques using radiation absorbing materials have some utility, techniques using radiation beams directed at the target tissue from various angles about a patient have come to be preferred. Such beams are often provided from a radiation source, e.g., x-ray photons or high-energy electrons, mounted on a rotating gantry, so that the radiation source revolves in a generally circular path while providing a beam of radiation directed generally at the isocenter of such a path. A patient is positioned within the circular path, preferably with the tumor located, to the extent possible, at the isocenter for receiving the maximum dose of radiation as the source is revolved. The cross-sectional shape and size of the radiation beam is typically varied as the source is positioned at different angles by rotation of the gantry in order to assure, to the extent possible, that the radiation is incident on the tumor itself and not on adjacent healthy tissue.

A number of techniques have been developed with the intention of providing for maximum absorption of radiation within the tumor while minimizing exposure of adjacent healthy tissue. Intensity-modulated radiation therapy (IMRT) was developed based on the principle that for a given tumor, there is a set of preferred ways to direct the radiation to it. More radiation can be sent through some beam angles than others and within the same beam angle, there are preferred locations through which the radiation is directed to the tumor. Computer-assisted treatment planning systems have been developed to take advantage of such preferred angles and locations, e.g., by varying the intensity of the radiation beam across the radiation fields, in order to accomplish better treatment regimens.

Consequently, intensity-modulated radiation therapy (IMRT) has been widely adopted as a new tool in radiation therapy to deliver high doses of radiation to the tumor while providing maximal sparing of surrounding critical structures. Both rotational and gantry-fixed IMRT techniques have been implemented clinically using dynamic multileaf collimation (DMLC) (1-6).

In gantry-fixed IMRT, multiple radiation beams at different orientations, each with spatially modulated beam intensities, are used (1-2, 4). The beams may be administered to the patient in a single transverse plane as the source revolves around the patient (coplanar) or may be shifted axially with respect to the patient (non-coplanar). Rotational IMRT, typically, administered by a continuously revolving source that is also moved axially along the patient, as it is currently practiced, mainly employs temporally modulated fan beams (3). Although the quality of IMRT treatment plans has steadily improved, the plans tend to be relatively complicated, which makes for a somewhat inefficient delivery of treatment. Consequently, labor-intensiveness has been one of the drawbacks of IMRT. Furthermore, in general, a large number of different complex field shapes is often needed, which also compromises the efficiency of the treatment and can result in an increased number of collimator artifacts (7). Nevertheless, while long-term clinical results of IMRT treatments are still limited, initial results appear very promising, and with increased use of IMRT, more encouraging results are emerging.

U.S. Pat. No. 5,818,902 to Yu teaches the use of overlapping multiple arcs to deliver modulated beam intensities around the patient which is called intensity-modulated arc therapy (IMAT). Delivery of the radiation during overlapping multiple arcs achieves modulated beam intensities at all angles around the patient (5-6). However, IMAT has not been widely adopted for clinical use. In IMAT, the intensity distributions are first optimized using a treatment planning system for tightly-spaced beam angles every 5-10 degrees all around the tumor. These intensity distributions are then approximated by a stack of uniform intensity segments with different cross sectional shapes. These stacks of uniform beam segments at all beam angles are then sequentially administered as the radiation source describes multiple rotational arcs while the beam cross sections are defined at each angular position by a multi-leaf collimator (MLC) with its leaves moved by a computer-programmed controller to provide a sequence of predetermined apertures.

The inverse planning procedures used to determine beam cross-sections and intensities when planning IMRT and IMAT treatments have typically required the user to predetermine the number of beams to use and their orientations. This limitation can significantly affect the quality of the treatment plans because the most preferred angle might be completely missed. Rotational IMRT does not have such problems since all angles are considered in the plan.

Furthermore, because the delivery of IMAT requires the use of multiple (4-11) arcs, each of which may take 1 to 2 minutes to deliver, the total treatment time is similar to that of fixed beam IMRT treatments. It is also relevant that, even when intensity distribution is determined for densely-spaced beam angles, i.e., 5 to 10 degrees, and sequenced for delivery in a limited number of multiple arcs, the resultant distribution of radiation absorption in the tumor can still only approximate that which would be provided by optimized beam intensities and cross-sections, because each of the planned beams may require significant variations that cannot be accommodated by the plan as executed by the equipment. As a result, the final IMAT plan is almost always degraded from the unconstrained optimized plan.

One attempt to solve this problem is a method for optimizing IMAT using Direct Aperture Optimization, in which the shape and weight of the apertures contained in one or more arcs are optimized simultaneously (8). A similar method (9), who showed that a single arc optimization using a method similar to Direct Aperture Optimization could generate satisfactory treatment plans for a simple case. In both methods, a limited number of beam angles were used to illustrate the principle. For complicated cases, single-arc optimization over a limited number of angles cannot generate plans that rival fixed-beam IMRT plans (8). Using such methods, it is prohibitive with today's technology to optimize the rotational delivery with more beam angles, because pencil beams must be calculated for all the beam angles (8-9).

Another concern with current radiation treatment planning methods is that no method developed hitherto can create a rotational IMRT plan that consistently rivals fixed beam IMRT without requiring beam intensity modulation. For simple cases it was demonstrated that a single optimized arc can yield results as good as those of fixed-field IMRT, while, for more complicated cases, such as head and neck cases with multiple targets, such an approach would not work well, and intensity modulation is required (8). Although allowing the planned dose rate to vary with gantry angle provides a new degree of freedom, such relaxation of a restraint is not sufficient in itself to establish that a single arc using the described optimization method can replace multiple-arc IMAT. Treatment planning using current optimization schemes requires intensity modulation consistently to rival fixed beam IMRT (10). Another method that can achieve very good efficiency utilizes optimization based on the direct aperture optimization method of Shepard et al (10). However, although the optimization starts with a limited number of fields and the connectedness of the field shapes can be ignored, as the optimization progresses, constraint to force the shape-connectedness will compromise the quality of he treatment plans. As the result, one would know what the ultimate plan quality is like.

Thus, there is a recognized need in the art for improved radiation therapy planning methods that enable greater efficiency in delivery of radiation therapy. More specifically, the prior art is deficient in methods and systems for single-arc dose radiation therapy. The present invention fulfills this long-standing need and desire in the art.

SUMMARY OF THE INVENTION

The present invention is directed to a method for designing a radiation treatment for a subject using single arc dose painting. The method comprises providing an unconstrained optimization map which supplies intensity profiles of densely-spaced radiation beams and aligning each intensity profile to a pair of multiple leaf collimation (MLC) leaves. A shortest path algorithm is applied to convert each pair of MLC leaves to a set of leaf aperture sequences, where each set of leaf aperture sequences forms a shortest path single arc thereof and each single arc of leaf apertures is connected to form a final treatment single arc, thereby designing the single arc dose painting radiation treatment. The present invention is directed to a related method further comprising delivering a continuous dose of radiation to the subject through each aperture during a single rotation along one or more final treatment single arc paths. The present invention is directed to another related method further comprising adjusting a shape of the aperture as a radiation dose delivery angle changes along the final treatment single arc. The present invention is directed to yet another related method for irradiating a tumor in a subject with the continuous dose of radiation through sets of multiple leaf collimation (MLC) aperture sequences during a single rotation along one or more of the treatment single arc paths. The present invention is directed a related method further comprising adjusting the aperture shape as described supra. Further still to these related methods the present invention is directed to a method further comprising repeating the irradiation step during another rotation along the treatment single arc path(s).

The present invention is directed further to a system for delivering radiation treatment using single arc dose painting. The system comprises a radiation source for generating a radiation beam, a multiple leaf collimator having a plurality of leafs for shaping the radiation beam, a structure for generating an unconstrained optimization map of intensity profiles of densely-spaced radiation beams, a structure for aligning each intensity profile to a pair of multiple leaf collimation (MLC) leaves, and a structure for applying a shortest path algorithm, said shortest path algorithm converting each pair of MLC leaves to a set of leaf aperture sequences forming a shortest path single arc thereof, such that the shortest path algorithm further connects each single arc of leaf apertures to form a final treatment single arc effective for single arc dose painting. The present invention is directed a related system where the shortest path algorithm further comprises adjusting the aperture shape as described supra.

The present invention is directed further still to a computer-readable medium tangibly storing an algorithm to determine a final single arc path for a single arc dose painting radiation treatment. The algorithm enables instructions to convert pairs of multiple leaf collimation (MLC) leaves to sets of leaf aperture sequences that form a shortest path single arc thereof, where the pairs of MLC leaves each are aligned to an intensity profile of densely-spaced radiation beams, and to connect each single arc of leaf apertures to form a final treatment single arc. The present invention is directed a related computer-readable medium where the shortest path algorithm further enables adjusting the aperture shape as described supra.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims.

The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE DRAWINGS

FIGS. 2A-2D illustrate the transformation of G' into ˆG (FIGS. 2A-2B) and the layered DAGs $G_{i1,i1+1}$, $G_{i1,i1+2}$, and $G_{i1,n}$ (FIG. 2C) where each vertex layer is represented by a vertical line segment, and the set of edges from one vertex layer to the next layer is represented by an arrow and the DAG Gi1 after merging the DAGs $G_{i1,i1+1}$, $G_{i1,i1+2}$, and $G_{i1,n}$ (FIG. 2D).

FIGS. 4A-4B illustrates sliding window leaf sequencing. In FIG. 4A the desired intensity profile is aligned with a leaf pair. FIG. 4B shows separated intensity profiles to be conformed by the leading (right) and training (left) leaves. FIG. 4C shows adjusted leaf traveling trajectories after considering the physical constraints of leaf travel.

FIGS. 7A-7B illustrate the planning of a single arc dose painting.

FIGS. 10A-10C illustrate a planned (FIGS. 10A-10B) and delivered (FIG. 10C) dose distribution for a complicated head and neck case with single arc dose painting.

DETAILED DESCRIPTION OF THE INVENTION

I. Definitions

Figure 1A:
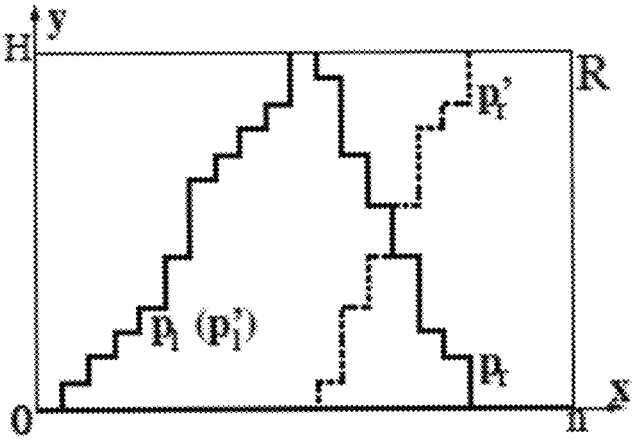
FIGS. 1A-1C illustrate how to flip the monotone decreasing path $p_r$ to a monotone increasing path $p'_r$ (FIG. 1A), how to flip two monotone decreasing paths $p_l$ and $p_r$ to two monotone increasing paths $p'_l$ and $p'_r$ (FIG. 1B) and how the xy-monotone region enclosed by the two paths $p'_l$ and $p'_r$ in FIG. 1B corresponds to a sequence of n vertical bars $B_1$ $B_2, \ldots, B_n$ (FIG. 1C). Note that after the flipping operations in FIGS. 1A-1B, neither the steepness nor the closeness constraint is violated, and $I_{i,pl,pr}=I_{i,p'l,p'r}$ holds for every i, which implies that the total error remains the same.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "about" refers to numeric values, including whole numbers, fractions, percentages, etc., whether or not explicitly indicated. The term "about" generally refers to a range of numerical values, e.g., +/−5-10% of the recited value, that one would consider equivalent to the recited value, e.g., having the same function or result. In some instances, the term "about" may include numerical values that are rounded to the nearest significant figure.

As used herein, the term "subject" refers to any recipient of single arc dose painting radiation treatment II. Present Invention In one embodiment of the present invention there is provided method for designing a radiation treatment for a subject using single arc dose painting, comprising providing an unconstrained optimization map which supplies intensity profiles of densely-spaced radiation beams; aligning each intensity profile to a pair of multiple leaf collimation (MLC) leaves; applying a shortest path algorithm to convert each pair of MLC leaves to a set of leaf aperture sequences, where the set of leaf aperture sequences form a shortest path single arc thereof; and connecting each single arc of leaf apertures to form a final treatment single arc, thereby designing the single arc dose painting radiation treatment.

Further to this embodiment the method comprises delivering a continuous dose of radiation to the subject through each aperture during a single rotation along one or more final treatment single arc paths. In another further embodiment the method comprises adjusting a shape of the aperture as a radiation dose delivery angle changes along the final treatment single arc.

In all embodiments the paths of more than one single arc may be non-coplanar. Also, the apertures may sweep back and forth along the single arc path during delivery of the radiation dose. In addition multiple leaf collimation may be dynamic.

In all embodiments sequencing leaf apertures may comprise one or more of a line segment approximation on component intensity profiles leaf position, weight optimization of apertures or optimization of leaf position and aperture weight. Also, the leaf aperture sequences in each set may have one or both of a different starting or ending leaf aperture. In addition, starting and ending positions of a leaf aperture trajectory may be fixed.

In another further embodiment of the present invention there is provided a method irradiating a tumor in a subject with the continuous dose of radiation through sets of multiple leaf collimation (MLC) aperture sequences during a single rotation along one or more of the treatment single arc paths. Further still to this further embodiment the method may comprise adjusting a shape of the aperture as a radiation dose delivery angle changes along the treatment single arc to keep the dose constant. Further still to both of these further embodiments the method may comprise repeating the irradiation step during another rotation along the treatment single arc path(s).

In another embodiment of the present invention there is provided a system for delivering radiation treatment using single arc dose painting, comprising a radiation source for generating a radiation beam; a multiple leaf collimator having a plurality of leafs for shaping the radiation beam; a structure for generating an unconstrained optimization map of intensity profiles of densely-spaced radiation beams; a structure for aligning each intensity profile to a pair of multiple leaf collimation (MLC) leaves; and a structure for applying a shortest path algorithm, where the shortest path algorithm converts each pair of MLC leaves to a set of leaf aperture sequences forming a shortest path single arc thereof and where the shortest path algorithm further connects each single arc of leaf apertures to form a final treatment single arc effective for single arc dose painting.

Further to this embodiment the shortest path algorithm may adjust a shape of the leaf aperture as a radiation dose delivery angle changes along the final treatment single arc. Also the shortest path algorithm may sequence leaf apertures via one or more of a line segment approximation on component intensity profiles leaf position, weight optimization of apertures or optimization of leaf position and aperture weight. In addition multiple leaf collimation may be dynamic.

In yet another embodiment of the present invention there is provided a computer-readable medium tangibly storing an algorithm to determine a final single arc path for a single arc dose painting radiation treatment, said algorithm enabling processor-executable instructions to convert pairs of multiple leaf collimation (MLC) leaves to sets of leaf aperture sequences that form a shortest path single arc thereof, where the pairs of MLC leaves are each aligned to an intensity profile of densely-spaced radiation beams; and connect each single arc of leaf apertures to form a final treatment single arc. Further to this embodiment the algorithm may enable instructions to adjust a shape of the leaf aperture as a radiation dose delivery angle changes along the final treatment single arc thereby keeping the dose constant. Also, the algorithm may sequence leaf apertures via one or more of a line segment approximation on component intensity profiles leaf position, weight optimization of apertures or optimization of leaf position and aperture weight.

Provided herein are methods and systems to plan and deliver a new rotational radiation therapy, identified herein as single arc dose painting (SADP), that can achieve a quality of treatment comparable to that of multi-arc IMAT using only one continuous rotation of the beam around the patient. The efficiency of such treatment delivery, as compared with that of IMAT, is significantly improved. Generally, the difference in the methods provided herein from prior methods is that the planning process is two steps. In the first step, intensity distributions are optimized over densely spaced beams, for example, on 36 or 72 fields. Because no delivery constraints are applied at the optimization step, the plan quality represents the ultimate. In the second step, the intensity modulated beams are sequenced into a single arc delivery, Planning a single arc capable of delivering the ultimately optimal radiation treatment is based on the recognition that the same intended dose to the tumor delivered by an aperture at a planned angle can be delivered by a slightly modified aperture from a slightly different angle. Consequently, a single rotation with dynamically varying apertures can achieve the same results as a procedure that delivers a plurality of intensity modulated fixed beams.

Furthermore, methods to convert the intensity or fluence patterns in the target, as optimized at fixed beam angles, into a single arc of beam rotation are also new and innovative. The inventive leaf sequencing method of the invention achieves an interconnected relationship of multiple leaf collimator (MLC) apertures so that the MLC leaves are not required to move large distances between adjacent angles of the planned treatment. By sweeping the apertures (windows) back and forth, the requirement of connectedness is much easier to meet.

Also, the dose rate can change among the angular intervals. However, such a change in dose rate is not a requirement. Typically, the aperture size and shape can be optimized to maintain a substantially constant dose rate throughout the entire treatment arc.

Within a planning interval, the apertures can have different weights, delivered either through dose rate variation with all apertures occupying the same angular range or delivered without dose rate variation by allowing the aperture with higher weights to be delivered over a larger angular range. That is, the method is applicable to machines with and without the ability to change dose rates during delivery.

For treatment of tumor or other sites amenable to radiation therapy where use of multiple non-coplanar arcs is beneficial, multiple non-coplanar arcs can be planned according to the methods of the invention. However, with single arc dose painting, it is typically unnecessary to have overlapping arcs. Accordingly, the dose overlap in the tumor is considered, rather than beam overlap in each beam direction as with current IMRT planning. This relies on the recognition that the same dose can be delivered to the tumor by two beam apertures of slightly different shapes directed at the tumor from two angular directions a few degrees apart.

Planning starts with an unconstrained optimization with a large number of beams evenly spaced, for example, every 5-10 degrees. Depending on the complexity of the optimal intensity distribution, different number of apertures and weights are initialized using a "sliding window" line-segment approximation. Because the initial shapes are derived from the "sliding window" principle, the apertures are interconnected. The shape and weights of these apertures are further optimized (fine-tuned) to improve the plan quality. To deliver these apertures in one arc, they are spaced within their own planning angular interval by moving the overlapping apertures to other beam angles within the interval. To ensure that the apertures deliver the same dose to the tumor as they are moved away from the planned angle, the aperture shapes are varied, depending on how many degrees they are moved from the planned angle. Adjusting the aperture shape is to faithfully create the intensity maps that were created under unconstrained optimization and to maintain the ultimate plan quality.

Intensity modulation is allowed during intensity optimization and more than one aperture shapes is allowed within each planning angular interval. As compared with IMAT, the apertures are spaced and adjusted within the planning angular interval rather than overlapped to be delivered by using multiple arcs. Because, as described herein, an entire treatment dose is delivered in a single rotation, the number of different apertures per planning angular interval can vary according to the complexity of the required intensity distribution.

As such, systems effective to deliver radiation to a tumor using single arc dose painting comprise those radiation delivery devices having suitable structures for radiation therapy of malignant tumors or other conditions responsive to such treatment. As is known in the art such devices comprise at least a source of radiation, amoveable, rotatable gantry, a multiple leaf collimator, e.g., a dynamic multiple leaf collimater, a platform for a subject receiving radiation therapy, and the necessary computer hardware and software, processor, memory and network or other connections necessary to run the device. In addition, the system comprises a module or structure, such as, but not limited to, a computer memory, a computer-readable memory or computer program to, storage device which is suitable to tangibly store and execute the algorithms described herein, such as, standard algorithms for intensity profile optimization and the novel short path algorithms provided herein.

The following examples are given for the purpose of illustrating various embodiments of the invention and are not meant to limit the present invention in any fashion.

EXAMPLE 1

Constrained Coupled Path Planning (CCPP)

In constrained coupled path planning, the starting and ending points of the sought paths are prespecified. Precisely, the constrained coupled path planning (CCPP) problem is: Given an n×H uniform grid $R_g$, a non-negative function $f$ defined on the integers in $\{1, 2, \ldots, n\}$, and positive integers $l_{start}$, $r_{start}$, $l_{end}$, $r_{end}$, c, and Δ (Δ≤H), find two noncrossing paths $p_l$ and $p_r$ of height H along the edges of $R_g$ to minimize the total error $\epsilon(p_l, p_r)$ $\Delta=\Sigma^n_{i+1}|l_{i,pl,pr}-f(i)|$, subject to the following constraints: (1) $p_l$ (resp., pr) starts at $(l_{start}, 0)$ (resp., $(r_{start}, 0)$) and ends at $(l_{end}, H)$ (resp., $(r_{end},H)$), (2) (the steepness constraint) both $p_l$ and $p_r$ are c-steep paths, and (3) (the closeness constraint) $|l_{i,pl,pr}-f(i)|\leq\Delta$ for all i=1, 2, . . . , n.

Figure 1B:
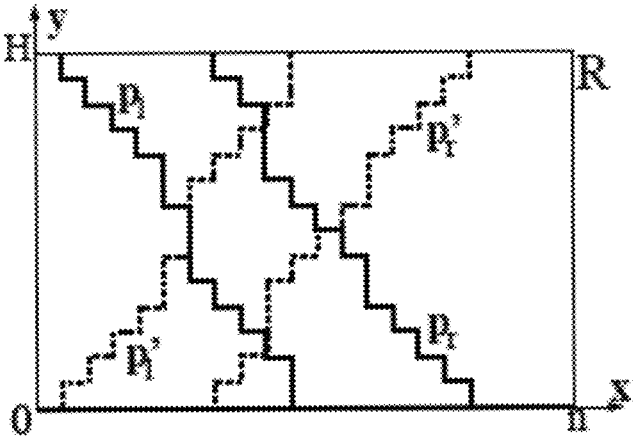
Figure 1C:
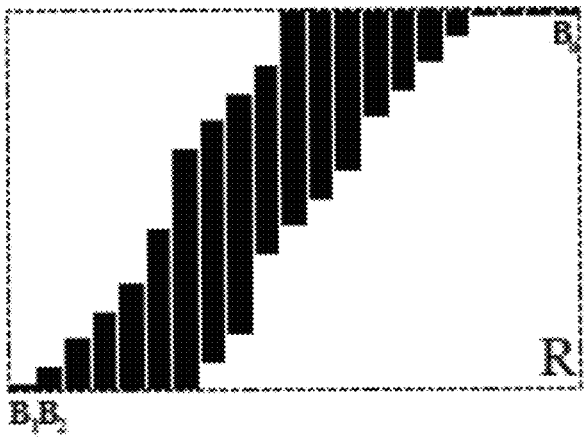

Without loss of generality, it is assumed that $l_{start}\leq l_{end}$ and $r_{start}\leq r_{end}$, so that the two sought paths $p_l$ and $p_r$ are both xy-monotone increasing paths. Otherwise, the CCPP problem can be transformed to a new CCPP problem that satisfies this condition. By flipping (FIGS. 1A-1B) one or both of the optimal paths for this new problem, two optimal paths are obtained for the original CCPP problem.

Algorithm for the Case where $l_{end}\geq r_{start}$

Figure 3A:
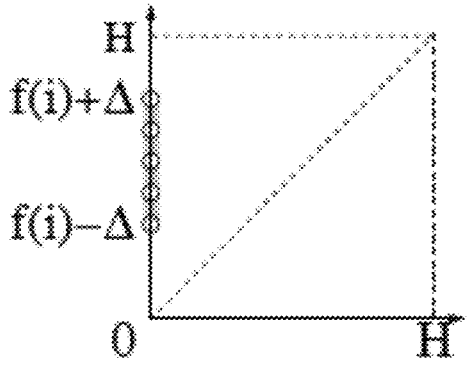
FIGS. 3A-3C illustrate the geometry of the vertex layer $L'_i$ of the DAG G' for $l_{start}<i\leq r_{start}$, $r_{start}<i\leq l_{end}$, and $l_{end}<i\leq r_{end}$. In each figure, all vertices in the vertex layer $L_i$ (or $L'_i$) are mapped to circled points on the 2-D plane; these points form all the lattice points in a convex polygon (possibly degenerated to a line segment) marked by the shaded area.
Figure 3B:
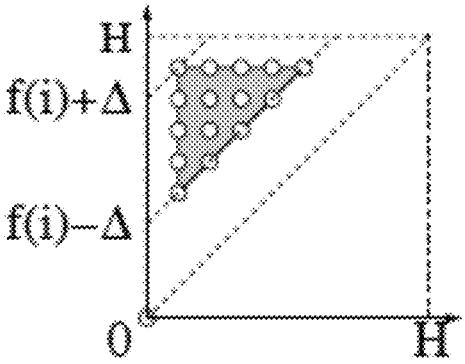
Figure 3C:
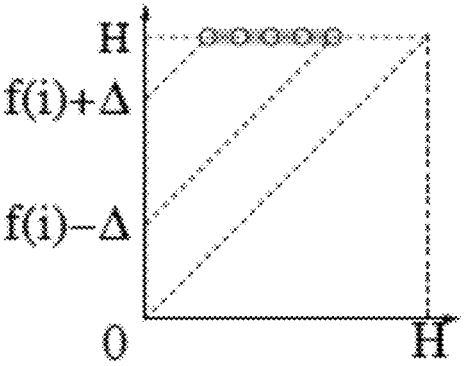

It is to be noted that the algorithm can be adapted easily to handle the other case in which $l_{end}<r_{start}$. The region $P(p_l, p_r)$ is a rectilinear xy-monotone polygon in $R_g$ and consists of a sequence of n vertical bars. Thus, the CCPP problem can be solved by transforming it to computing a shortest path in a directed acyclic graph, DAG G'. The DAG G' (FIG. 2A-2D) also contains a source s, a sink t, and n layers of vertices, $L'_1, L'_2 \ldots, L'_n$, which are defined as follows to satisfy the additional geometric constraints of the CCPP problem:

and, further, the vertices and edges of G0 have geometric properties similar to those of dominated sets (FIGS. 3A-3C). Such similar dominated sets may be D(H,H), D(α,H) (0<α<H), D(0,H), D(α,β) (0<α≤β<H) D(0,β) (0<β<H), and D(0, 0). Thus the shortest path computation can be sped up and the CCPP algorithm takes O(nHΔ) time.

EXAMPLE 2

Computing the Complete Set of all CCPP Problem Instances

Overview of the Algorithm

Given f, n, H, Δ, and c, CCPP problem instances are solved on f, n, H, Δ, c, $l_{start}$, $r_{start}$, $l_{end}$, and $r_{end}$ for all possible combinations of $l_{start}$, $r_{start}$, $l_{end}$, and $r_{end}$. Without loss of generality, only those combinations which satisfy $l_{start}\leq l_{end}$ and $r_{start}\leq r_{end}$ are considered. All problem instances are classified into two subsets $S_1$ and $S_2$, with $S_1$ (resp., $S_2$) containing those with $l_{end}\geq r_{start}$ (resp., $l_{end}<r_{start}$).

Solving all CCPP Instances in $S_1$

It is to be noted that this approach can be adapted easily to solve all instances in $S_2$. Since $0\leq l_{start}\leq r_{start}\leq l_{end}\leq r_{end}\leq n$, there are totally $N=\Theta(n^4)$ problem instances, denoted by $l_1$, $l_2$, . . . , $l_N$. Let $l^{(k)}_{start}$, $r^{(k)}_{start}$, $l^{(k)}_{end}$, and $r^{(k)}_{end}$ be the corresponding specification for the problem instance lk. An instance $l_k$ (1≤k≤N) corresponds to a shortest path problem on a vertex-weighted DAG, denoted by $G'_k$, of O(nHΔ) vertices and $O(nH^2\Delta^2)$ edges. The key observation is that $G'_k$ can be transformed into an edge-weighted DAG, denoted by $\hat{G}_k$, with only O(Δ) vertices and $O(\Delta^2)$ edges.

The algorithm consists of two main steps. First, prepare the weights of all edges in $\hat{G}_1$, $\hat{G}_2$, . . . , and $\hat{G}_N$ ($O(\Delta^2)$ edges for each $\hat{G}_k$). The weights of all the $O(n^4\Delta^2)$ edges are implicitly computed and stored in a batch fashion, in totally $O(n^2H^2)$ time, such that for any edge, its weight can be reported in O(1) time. Second, a shortest path is computed in $\hat{G}_1$, $\hat{G}_2$, . . . , and $\hat{G}_N$, respectively. It is shown that each $\hat{G}_k$ (1≤k≤N) is a DAG satisfying the Monge property (1-2,4). Since the weight of any edge can be obtained in O(1) time, a shortest path in $\hat{G}_k$ takes only O(Δ) time to compute. The algorithm thus takes $O(n^2H\Delta^2+n^4\Delta)$ time, improving the straightforward $O(n^5H\Delta)$ time algorithm, i.e., applying the CCPP algorithm $N=O(n^4)$ times) by a factor of min{nH, $n^3/\Delta$}.

The Graph Transformation

For fixed $l_{start}$, $l_{end}$, $r_{start}$, and $r_{end}$ ($0\leq l_{start}\leq r_{start}$ $l_{end}\leq r_{end}\leq n$), let l be the corresponding CCPP problem instance and G'=(V(G'),E(G')) be the vertex-weighted DAG defined in Example 1 for solving l. For u is an element of V(G), denote its weight by ω'(u). For a path p in G', the weight ω'(p) of p is defined as $\omega'(p)=\Sigma_{u\ is\ element\ of\ p}\ \omega'(u)$. For u, v is an element of V(G'), denote by π'(u, v) a shortest u-to-v path in G'.

$$L'_i\begin{cases}\{([\alpha,\ \beta])^{(i)}\ |\ \alpha=\beta=0 \text{ and } |\beta-\alpha-f(i)|<\Delta\} & \text{if } 1<=i<=I_{start}\\ \{([\alpha,\ \beta])^{(i)}\ |\ 0=\alpha<\beta<=H-c \text{ and } |\beta-\alpha-f(i)|<\Delta\} & \text{if } I_{start}<i<=r_{start}\\ \{([\alpha,\ \beta])^{(i)}\ |\ c<=\alpha<=\beta<=H-c \text{ and } |\beta-\alpha-f(i)|<\Delta\} & \text{if } r_{start}<i<=I_{endt}\\ \{([\alpha,\ \beta])^{(i)}\ |\ c<=\alpha<\beta=H \text{ and } |\beta-\alpha-f(i)|<\Delta\} & \text{if } I_{end}<i<=r_{end}\\ \{([\alpha,\ \beta])^{(i)}\ |\ \alpha=\beta=H \text{ and } |\beta-\alpha-f(i)|<\Delta\} & \text{if } r_{end}<i<=n\end{cases}\qquad \text{Eq. (1)}$$

The weight of a $[\alpha, \beta]^{(i)}$ is defined as $\omega'([\alpha, \beta]^{(i)})=\beta-\oplus-f(i)|$ and the edges of G' are defined based on the same domination relation D(•,•). A shortest s-to-t path in G corresponds to an optimal solution for the CCPP problem An edge-weighted directed graph $\hat{G}=(V(\hat{G}),E(\hat{G}))$ is constructed from G' as follows (FIGS. 2A-2B). The vertex set $V(\hat{G})$ is a subset of $V(\hat{G})$, and consists of two dummy vertices s and t and four vertex layers:

$$\hat{L}_1 \triangleq L'_{i_{start}},\ \hat{L}_2 \triangleq L'_{r_{start}},\ \hat{L}_3 \triangleq L'_{l_{end}+1},\ \text{and}\ \hat{L}_4 \triangleq L'_{r_{end}+1}.$$

The edge set E(ˆG) is simply $$\cup_{t=1}^{3}(\hat{L}_t \times \hat{L}_{t+1}) \cup (\{s\} \times \hat{L}_1) \cup (\hat{L}_4 \times \{t\}).$$

Thus, the subgraph of ˆG between any two consecutive vertex layers is a complete bipartite graph. For each edge (u, v) is an element of E(ˆG), a weight $\hat{\omega}(u, v)=\omega'(\pi'(u, v))-\omega'(u)$ is assigned to it, i.e., the weight of a shortest u-to-v path in G' minus the vertex weight of u. For convenience, $\hat{\omega}(u, v)^{\Delta}=+\infty$ if there is no path from u to v in G'.

ˆG is an edge-weighted DAG and has O(Δ) vertices and $O(\Delta^2)$ edges (by the definition of $L'_i$ in Example 1). Define the weight ˆω(p) of a path p in ˆG as $\hat{\omega}(p)=\Sigma_{e \text{ is an element of } p}\ \hat{\omega}(e)$. A shortest s-to-t path in G' is closely related to a shortest s-to-t path in ˆG. In fact, it is not difficult to show that if $p'=s\rightarrow u_1\rightarrow u_2\rightarrow \ldots \rightarrow u_n\rightarrow t$ is a shortest s-to-t path in G', then $\hat{p}=s\rightarrow u_{lstart}\rightarrow u_{rstart}\rightarrow U_{lend+1}\rightarrow U_{rend+1}\rightarrow t$ is a shortest s-to-t path in ˆG, with $\hat{\omega}(\hat{p})=\omega'(p'')$ This is due to the optimal-substructure property of shortest paths, i.e., any subpath of a shortest path is also a shortest path. Moreover, if $s\rightarrow v_2\rightarrow v_3\rightarrow v_4\rightarrow t$ is a shortest s-to-t path in ˆG, then $s \xrightarrow{\pi'(s,v_1)} v_1 \xrightarrow{x'(v_1,v_2)} v_2 \xrightarrow{x'(v_2,v_3)} v_3 \xrightarrow{x'(v_3,v_4)} v_4 \xrightarrow{x'(v_4,t)}$ is a shortest s-to-t path in G'.

Before explaining why the vertex layers $L'_{lstart}$, $L'_{rstart}$, $L'_{lend+1}$, and $L'_{rend+1}$, from G' for the construction of ˆG were chosen, Equation (1) must be reviewed. Observe that if i is fixed and $l_{start}$, $r_{start}$, $l_{end}$, and $r_{end}$ are temporarily viewed as parameters, then Equation (1) implies that the i-th vertex layer in any G ($1\le k\le N$) is in exactly one of five possible states, denoted by $\Lambda_i^{(I)}$, $\Lambda_i^{(II)}$, $\Lambda_i^{(III)}$, $\Lambda_i^{(IV)}$, and $\Lambda_i^{(V)}$, e.g., $\Lambda_i^{(I)}$ if $1\le i\le l_{start}$). For a fixed k ($1\le k\le N$), in the DAG $G'_k$, the i-th vertex layer L is of type I if $L=\Lambda_i^{(I)}$. The type II, III, IV, and V vertex layers are defined similarly.

Clearly, in the DAG G', all vertex layers between s and $L'_{lstart}$, $L'_{lstart}$ and $L_{rstart}$, $L''_{rstart}$ and $L'_{lend+1}$, $L'_{lend+1}$, and $L'_{rend+1}$, and $L'_{rend+1}$ and t are of type I, II, III, IV, and V, respectively (FIG. 2A). This implies an interesting property: For any edge (u, v) of ˆG, all vertex layers between u and v in G' are of the same type. As will be shown, this property plays a key role in speeding up the computation of the weights of all edges in the transformed DAGs $\hat{G}_1$, $\hat{G}_2$, . . . $\hat{G}_N$. It should be pointed out that for one DAG G', although ˆG is of a much smaller size than G', the weights of the edges of ˆG are costly to compute. Thus transforming G' to ˆG will not yield a faster algorithm for solving a single CCPP problem instance.

Computing the Edge Weights for all Transformed DAGs

It is demonstrated herein how to compute the weights of all edges in the transformed DAGs $\hat{G}_1$, $\hat{G}_2$, . . . , $\hat{G}_N$. Recall that the weight of an edge in $\hat{G}_k$ corresponds to a one-pair shortest path problem instance on $G'_k$. Since every $\hat{G}_k$ has $O(\Delta^2)$ edges, there are in total $O(n^4\Delta^2)$ edges in $\hat{G}_1$, $\hat{G}_2$, . . . , $\hat{G}_N$, corresponding to $O(n^4\Delta^2)$ one-pair shortest path problem instances.

It is stated that the $O(n^4\Delta^2)$ edges actually correspond to only $O(n^2\Delta^2)$ distinct one-pair shortest path problem instances. For any k that is an element of {1, 2, . . . , N} and for any edge (u, v) that is an element of $\hat{G}_k$, denote by SP(u, v, k) the corresponding one-pair shortest path instance, i.e., finding a shortest u-to-v path in $G'_k$. Considering the indices of the vertex layers in which u and v lie in $\hat{G}_k$ respectively, there are five cases. Only the most typical case, in which u (resp., v) lies in the 2nd (resp., 3rd) layer of $\hat{G}_k$ is discussed. For this case, let $i_1=r^{(k)}_{start}$ and $i_2=l^{(k)}_{end+1}$; then u is an element of $\Lambda^{II}_{i1}\subset V(G'_k)$, v is an element of $\Lambda^{IV}_{i2}\subset V(G'_k)$, and all vertex layers between u and v in $G'_k$ are of type III (FIG. 2A). Let $G_{i1,i2}$ be a layered DAG whose vertices consist of the vertex layers $\Lambda^{II}_{i1}$, $\Lambda^{III}_{i1+1}$, $\Lambda^{III}_{i1+2}$, . . . , $\Lambda^{III}_{i2-1}$, and $\Lambda^{IV}_{i2}$, in this order, and whose edges are defined based on the same domination relation D(•,•).

Clearly, SP(u, v, k) is equivalent to finding a shortest u-to-v path in $G_{i1,i2}$. Since $i_i$ (resp., i2) ranges from 1 to n, $G_{i1,i2}$ has $O(n^2)$ possible choices. Note that u (resp., v) belongs to the layer $\Lambda^{II}_{i1}$ (resp., $\Lambda^{IV}_{i2}$), which contains O(Δ) vertices for any $i_i$ (resp., $i_2$). It follows that SP(u, v, k) has $O(n^4\Delta^2)$ possible choices for the case where u (resp., v) lies in the 2nd (resp., 3rd) layer of $\hat{G}_k$. Other cases can be analyzed similarly. Since there are five cases, SP(u, v, k) has $O(n^2\Delta^2)\times O(1)=O(n^2\Delta^2)$ possible choices in total.

Since there are only $O(n^2\Delta^2)$ distinct one-pair shortest path problem instances, it is preferred to implicitly compute and store the weight of each edge of $\hat{G}_1$, $\hat{G}_2$, . . . , $\hat{G}_N$. More specifically, distinct one-pair shortest path instances are solved and the corresponding shortest paths along with their lengths are stored, so that given an edge (u, v) of any $\hat{G}_k$, its weight can be reported in O(1) time.

It is demonstrated how to solve the $O(n^2\Delta^2)$ distinct one-pair shortest path problem instances in a batch fashion. First a set of one-pair shortest path instances are combined into one single-source shortest path problem instance. Second, a set of single-source shortest path instances are solved in one shot by "merging" the underlying DAGs into one DAG of a comparable size. This approach is illustrated by showing how to solve the one-pair shortest path instances in $G_{i1,i2}$ (as defined in the previous paragraph) for all $i_1$, $i_2$. Each instance is specified by a source vertex u is an element of $\Lambda^{II}_{i1}$ and a destination vertex v is an element of $\Lambda^{IV}_{i2}$. Recall that $G_{i1,i2}$ contains the vertex layers $\Lambda^{II}_{i1}$, $\Lambda^{III}_{i1+1}$, $\Lambda^{III}_{i1+}$, . . . , $\Lambda^{III}_{i2-1}$, and $\Lambda^{IV}_{i2}$, For a fixed $i_1$, the layered DAGs $G_{i1,i2}$, for all $i_2=i_1+1$, . . . , n, can be merged into one DAG, simply denoted by $G_{i1}$ (FIGS. 5C-5D). For any vertex u is an element of $\Lambda^{II}_{i1}$, its single-source shortest paths can be computed in $G_{i1}$, in O(nHΔ) time as in the CCPP algorithm. Since $|\Lambda^{II}_{i1}|=O(\Delta)$ and $i_1$ ranges from 1 to n, the one-pair shortest path instances in $G_{i1}$,i2 can be solved for all $i_1$, $i_2$, in $O(nH\Delta)\times O(n)\times O(\Delta)=O(n^2\Delta^2)$ time.

Shortest Path Computation on the Transformed DAGs

The algorithm for computing a shortest path in the DAG ˆG as defined as defined above is presented. The key idea is to show that ˆG satisfies the Monge property [1, 2, 4], and thus a shortest path in ˆG can be computed by examining only a small portion of its edges.

Consider the vertex layers $\hat{L}_2$ and $\hat{L}_3$ of ˆG. Clearly, $\hat{L}_2=L'_{rstart}=\{[\alpha, \beta]^{(rstart)}0=\alpha<\beta<=H-c \text{ and } |\beta-\alpha-f(rstart)|\le\Delta\}=\{[0, \beta]^{(rstart)}|0<\beta<=H-c \text{ and } |\beta-f(rstart)|\le\Delta\}$). Thus $\hat{L}_2$ can be written as $\hat{L}_2=\{u_1, u_2, \ldots, u_{|\hat{L}2|}\}$, where $u_k=[0, \beta_k]^{(rstart)}(1\le k\le|\hat{L}_2|)$ and $0<\beta_1<\beta 2< \ldots <\beta_{|\hat{L}2|}\le H-c$. Similarly, write $\hat{L}_3$ as $\hat{L}_3=\{v_1, v_2, \ldots, v_{|L3|}\}$, where $v_k=[_k, H]^{(lend+1)}(1\le k\le|\hat{L}_3|)$ and $c\le\alpha_1<\alpha_2< \ldots <\alpha_{|\hat{L}3|}<H$. The following lemma shows the properties of the edges from the vertices on $\hat{L}_2$ to $\hat{L}_3$ in ˆG.

Lemma: (A) Let $u_i$ (resp., $v_j$) be a vertex on $\hat{L}_2$ (resp., $\hat{L}_3$) of ˆG, with $1\le i\le|\hat{L}_2|$ (resp., $1\le j\le|\hat{L}_3|$). If $\hat{\omega}(u_i, v_j)=1$, then for any j'<j (resp., i'>i), $\hat{\omega}(u_i, v_j)=\infty$(resp., $\hat{\omega}(u_i, v_j)=\infty$). (B) Let $u_i$, $u_{j'}$ (resp., $v_j$, $v_{j'}$) be two vertices on $\hat{L}_2$ (resp., $\hat{L}_3$) of ˆG, with $1\le i<i'\le|\hat{L}_2|$ (resp., $1\le j<j'\le|\hat{L}_3|$). If both edges $e_1=(u_i, v_{j'})$ and $e_2=(u_{i'},v_j)$ have finite weights, then edges $e_3=(u_i, v_j)$ and $e_4=(u_{i'}, v_{j'})$ also both have finite weights. Moreover, $\hat{\omega}(e_3)+\hat{\omega}(e_4)\ \hat{\omega}(e_1)+\hat{\omega}(e_2)$.

The lemma implies that the matrix A of size $|\hat{L}_2|\times|\hat{L}_3|$, with $=\hat{\omega}(u_i, v_j)$, is a Monge matrix. Note that for any i and j, $\hat{\omega}(u_i, v_j)$ can be reported in O(1) time as described above. Thus in $\hat{G}$, once the shortest paths from s to all vertices in $\hat{L}_2$ are computed, using the Monge matrix multiplication algorithms [1, 2, 4], the shortest paths from s to all vertices in $\hat{L}_3$ can be computed in $O(\Delta)$ time. Observe that outside the subgraph of $\hat{G}$ between the vertex layers $\hat{L}_2$ and $\hat{L}_3$ (FIG. 2B), there are only $O(\Delta)$ edges of $\hat{G}$. Hence a shortest s-to-t path in $\hat{G}$ can be computed in $O(\Delta)$ time. Thus, the following theorem is:

Given a non-negative function $f$ defined on $\{1, 2, \ldots, n\}$ and positive integers c, H, and $\Delta(\Delta \leq H)$, the complete set of the CCPP problem instances is computable in $O(n^2H^2+n4)$ time.

EXAMPLE 3

Unconstrained Intensity Optimization in Single-arc Dose Painting

The first planning step for single arc dose painting is unconstrained intensity optimization. Different algorithms can be used for achieving this step (11-13). Suitable algorithms are available in the relevant literature (8,10). As with IMAT, an arc is approximated with multiple fixed radiation beams evenly spaced every 5-10 degrees (5).

EXAMPLE 4

Leaf-sequencing in Single-arc Dose Painting

Step two in single-arc dose painting is the conversion of the optimized beam intensities into connected field apertures. The goal is to find a set of connected field shapes that when delivered dynamically based on linear interpolation between the apertures, will result in minimum discrepancy to the optimized intensity profile. For leaf sequencing, a hybrid approach has been developed. For simple cases the method called line segment approximation on component intensity profiles is appropriate. For more complicated cases, leaf position and aperture weight optimization and leaf position and aperture weight optimization may be used.

Line Segment Approximation to Component Intensity Profiles

This method is based on a "sliding window" technique. Recognizing that any intensity pattern can be delivered by sliding a varying aperture in either direction, each of the intensity patterns can be converted into "sliding window" dynamic control points. The only constraint to ensure the interconnectedness of the intensity patterns is that in the next interval, the direction of the "sliding window" has to be in the opposite direction. Accordingly, the apertures defined by the multi-leaf collimator (MLC) sweep back and forth, completing one cycle in every two intervals.

The conversion from fluence distributions to MLC "sliding window" delivery is illustrated by FIGS. 4A-4B. For a given arbitrary intensity distribution aligned with a pair of opposing leaves, such as that shown in FIG. 4A, initially, a separation is made between the portion to be delivered by the leading leaf (right leaf) and that to be delivered by the trailing leaf (left leaf). With the radiation source turned on, for a fixed left leaf position, moving the right leaf towards the right will create a negative gradient. Likewise, for a fixed right leaf position, moving the left leaf towards the right will create a positive intensity gradient. Therefore, the method first finds the points that separate the positive and negative gradients, as illustrated by the vertical lines. Then positive gradient portions are to the trailing profile and inverted negative gradient portions to the leading profile as shown on FIG. 4B. The vertical axis represents beam intensity in radiation monitor units (MUs), which is also time for a given machine dose rate. With this separation, the profile may be defined as follows:

Original profile=Trailing Profile−Leading profile.

The separated profiles become the leading and trailing leaf positions as functions of time. If both leaves are moved according to FIG. 1B, the desired intensity profile will be created.

Inspection of FIG. 4B, reveals that for both leaves, there will be sections where the leaves are required to change positions with no elapsed time (the flat portions of the profiles). Accordingly, in order to make the dose delivery physically achievable, the minimum gradient required for leaf travel (governed by the maximum leaf traveling speed) is added to the flat portions, while the same amount is added to the other profile so that the difference between the two profiles is kept substantially constant (FIG. 4C). When this intensity profile is delivered, the apertures of varying width formed by both leaves will move smoothly from the left to the right. Such smooth motion is the origin of the term "sliding window technique". The left leaf can alternatively be considered to be the leading leaf and the right leaf to be the trailing leaf, thereby delivering the same intensity distribution by sliding the "window" from the right to the left.

With the current art of dynamic MLC leaf sequencing, the control-points are generated by evenly dividing the total monitor units (MUs) required by the number of segments, which is normally relatively large (~50). Rather than a pure "sliding window" leaf-sequencing as described in FIGS. 4A-4B, it is also possible to sequence the optimized intensity maps in a "sliding window" fashion using a graph algorithm known and standard in the art. Because the treatment apparatus, linac and MLC, performs the linear interpolation automatically, accurate delivery is ensured if the vertices that join two lines of different slopes are used as control points. Therefore, the gradient turning positions of the original intensity profile (the intercepts of the vertical lines with the profiles) are used as the initial estimations of the control points. In essence, the original component intensity profiles are approximated with connected line segments. These initial control points are used as the input to the next step of the leaf sequencing process.

As indicated in FIGS. 4A-4B, the apertures selected from the sliding window leaf sequence are naturally interconnected within each planning interval. The apertures within each interval will move either left to right or right to left. To make it easier to connect all intervals into one arc, the apertures are sequenced in such a way that: 1) the MLC leaves move in opposite directions in any two neighboring angular intervals; and 2) the two aperture shapes connecting any two angular intervals do not violate the physical constraints of the MLC (i.e., the shapes are not so drastically different as to require large MLC movements). Because any intensity map can be delivered dynamically in either left-to-right or right-to-left leaf motion, the direction of MLC motion alternates between neighboring beams and the aperture shape connectivity is considered throughout the arc. As a result, the shape-varying beam aperture (or "dynamic window") slides back and forth while the gantry rotates around the patient.

Leaf Position and Aperture Weight Optimization

One of the concerns presented by method using line segment approximation to component intensity profiles is that for complex intensity distributions, using this method alone may result in a plan with very high machine beam-on times and may requires too many control points to maintain a very close dose conformity. Thus for more complicated cases, two alternative, and somewhat more complex, methods can be used, as described below.

Observe that during the delivery of a set of densely-spaced intensity patterns, each pair of MLC leaves will deliver a set of densely-spaced intensity profiles that are aligned with this leaf pair. The method comprises the following key steps:

First, for every pair of MLC leaves, each of its aligned intensity profiles is converted into a set of k leaf openings using a geometric k-link shortest path algorithm with equal beam-on times that incurs the minimum error. Second, the leaf openings for the same pair of MLC leaves are connected together to form a single-arc of leaf openings using a geometric shortest path algorithm that ensures a smooth transition between adjacent leaf openings while minimizing the error incurred. Third, the single-arcs for each pair of MLC leaves are then combined to form the final single-arc treatment plan.

Figure 5B:
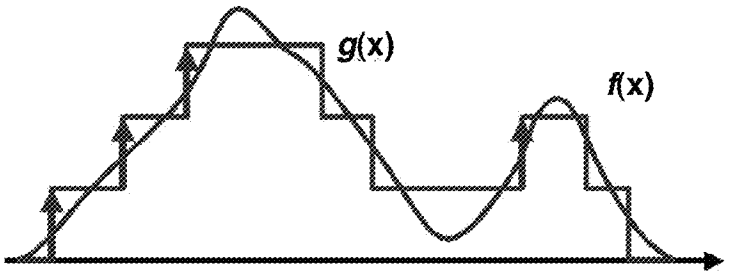
FIGS. 5A-5D illustrate steps of the shortest path graph algorithm for converting an intensity profile into k MLC leaf openings with the minimum error.
Figure 5A:
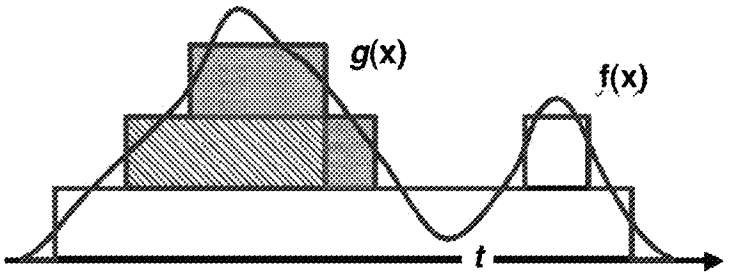
Figure 5D:
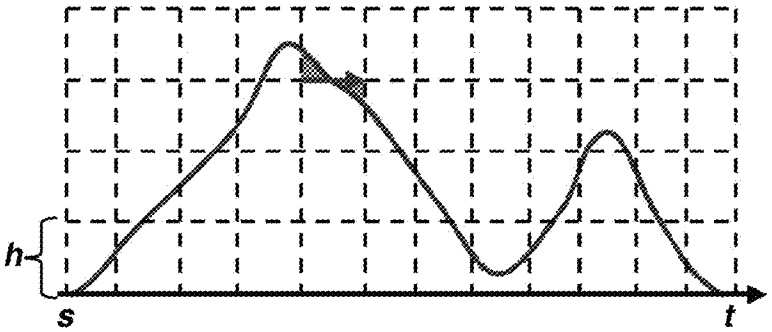
Figure 5C:
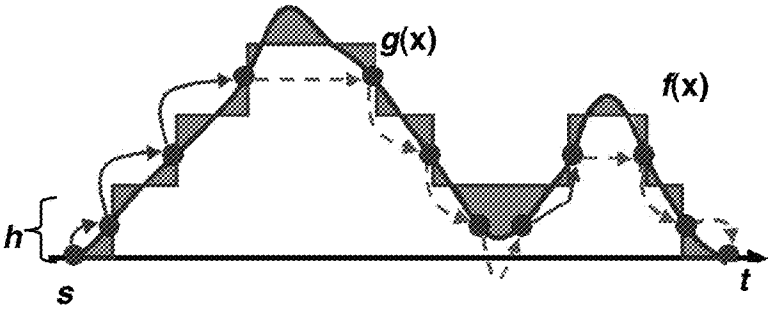

FIGS. 5A-5D illustrate the key idea of this step. In FIG. 5A, the optimized fluence profile is represented by the functional curve $f(x)$ and the resulting simplified profile is the rectilinear functional curve $g(x)$ that is deliverable by $k=4$ leaf openings with equal beam-on. The error here is the integral of the absolute difference between the two functions, $\int|f(x)-g(x)|dx$ (the shaded area in FIG. 5C). In FIG. 5A, each leaf opening is represented by a rectangle whose left and right ends are the positions of the MLC leaf pair and whose height is its beam-on time. The simplified intensity profile is created by "stacking up" these rectangles. Since all the leaf openings have the same beam-on time, i.e., the rectangles representing the leaf openings all have the same height, the resulting profile $g(x)$ can have up to k upward edges and k downward edges, if we traverse the profile curve from left to right (FIG. 5B). This problem can be solved by searching for an optimal k-weight path in a graph capturing the geometry of the problem; the total cost of the path represents the error between the simplified profile and the input profile, and its weight indicates how many leaf openings are needed to create the simplified profile. FIG. 5C illustrates such a k-weight path, where the k upward edges are highlighted in red (solid if black and white) and the error is the area sum of the shaded regions.

To find such a k-weight path, a directed graph G is constructed as in FIG. 5D. Specifically, for each possible height h of the rectangles, a grid structure is imposed, whose vertical edge lengths are h and horizontal edge lengths are of the resolution size of the given intensity patterns. Each grid node is a vertex of the graph G. The lower leftmost grid node is the source vertex s of G, and the lower rightmost node is the sink vertex t. For any horizontal grid edge, we put an edge in G from left to right with a zero weight and a cost that is the error incurred when this edge is used by the resulting profile (FIG. 5D) for a horizontal edge and its cost, i.e., the shaded area). For each vertical grid edge, we put in G an upward edge with a unit weight and a downward edge with a zero weight. Observe that a k-weight optimal s-to-t path in G thus constructed yields a desired simplified profile. This optimal path problem can be solved by the constrained shortest path algorithm.

The k-link path algorithm above will convert each intensity profile into a simplified profile that can be deliverable by k leaf openings. For each simplified profile, there are potentially k! ways to break it up into leaf openings. In this algorithm, break each simplified intensity profile is broken into a set of canonical leaf openings. Specifically, a set of leaf openings is called canonical if only if for any two leaf openings $[l_i, r_i]$ and $[l_j, r_j]$ (where and $l_i$ and $l_j$ denote the left leaf positions, and $r_i$ and $r_j$ denote the right leaf positions), either $l_i \le l_i, r_j \le r_j$, or $l_i \ge l_i$, $r_j \ge r_j$. Intuitively, a set of canonical leaf openings can be sorted from left to right.

Figure 6A:
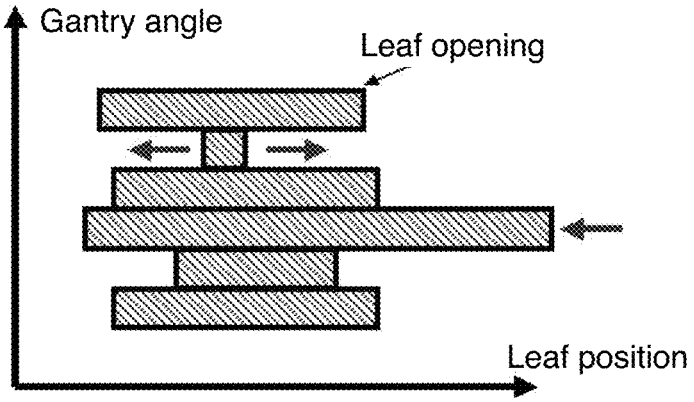
FIGS. 6A-6C illustrate a step of the shortest path graph algorithm for adjusting a one-dimensional IMAT arc.
Figure 6B:
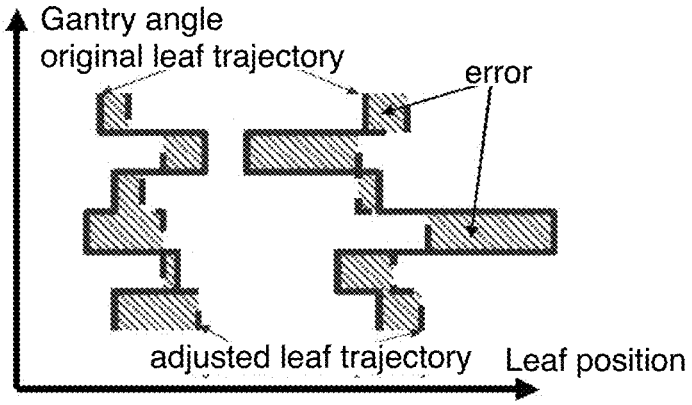
Figure 6C:
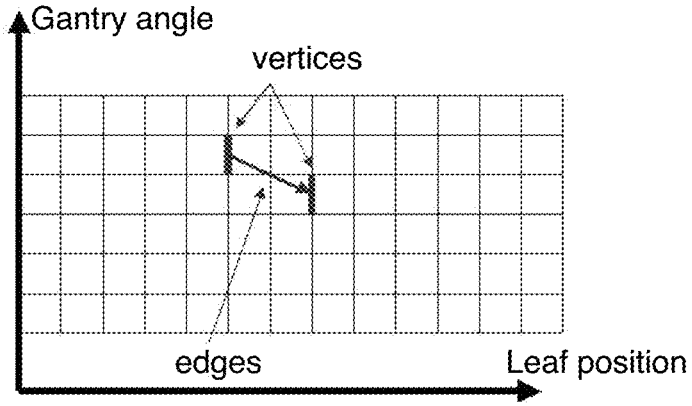

FIGS. 6A-6C illustrate the key concept for the second step, i.e., for combining the canonical leaf openings into arcs. When combining the leaf openings to form a single-arc, for each pair of leaves, its single-arc can be viewed as two curves, each representing the leaf trajectory as a function of the leaf position with respect to the gantry angles. The solid curves in FIG. 6B show the corresponding leaf trajectories of the single-arc illustrated in FIG. 6A. If this single-arc is not deliverable under the maximum leaf speed constraint, the arc has to be adjusted to make it deliverable while minimizing the error incurred by the adjustment.

Geometrically, the effect of the adjustment is to deform the original leaf trajectories into two new leaf trajectories. FIG. 6B gives such an adjustment where the original solid curves are changed to the dashed ones. The error is the area sum of the shaded regions. Since each leaf trajectory is a function of the leaf position with respect to the gantry angles, it can be viewed as a path of leaf positions along the gantry angle direction. This implies that the above adjustment problem can be solved by modeling it as a shortest path problem, in which the cost of a path is the error of the adjustment. FIG. 6C shows the graph construction. Each possible leaf position is a vertex, and two vertices for adjacent gantry angles are connected by an edge if they satisfy the maximum leaf speed constraint. Each vertex has a cost for the error incurred when adjusting the corresponding original leaf position for its gantry angle using that vertex. Geometrically, this error corresponds to a shaded region in FIG. 6B. Hence, the problem of adjusting a single arc as originally planned into a deliverable arc becomes a shortest path problem.

The spacing of the apertures within each interval is also straightforward. This is because the apertures obtained for each angular interval can sorted from left to right. The angular interval can be evenly divided the by the number of apertures used to reproduce the intensity distribution. The apertures can be sequenced in such a way that: 1) the MLC leaves move in opposite directions in any two neighboring angular intervals; and 2) the two aperture shapes connecting any two angular intervals do not violate the physical constraints of the MLC, i.e., they are not so drastically different as to require large MLC movements. As the result, the shape-varying beam aperture slides back and forth while the gantry rotates around the patient. Since the apertures for different angular intervals are obtained with different dose rates, this single arc plan may require dose rate changes during the delivery.

Leaf Position and Aperture Weight Optimization

In some clinical cases, it may be desirable to construct a series of single-arc plans that represent a tradeoff between machine beam-on times and error between the delivered fluence and prescribed ideal fluences. In such a case, in the event that each of the previously described two methods fails to give a high quality plan, the following method described in this section may be used.

Consider FIGS. 7A-7B, and, for simplicity, assume that the MLC consists of only one pair of leaves. FIG. 7A shows a sample single-arc plan, where the red curve represents the left leaf trajectory and the blue curve represents the right leaf trajectory. Note that, since, in a single-arc plan, the MLC keeps moving as the gantry rotates 360° around the patient at constant speed, the leaf trajectory is actually a functional curve between gantry angle and MLC leaf positions. For each small angular interval Δθ (typically)5°-10°, the portions of the leaf trajectories deliver a fluence profile (FIG. 7B).

Figure 8A:
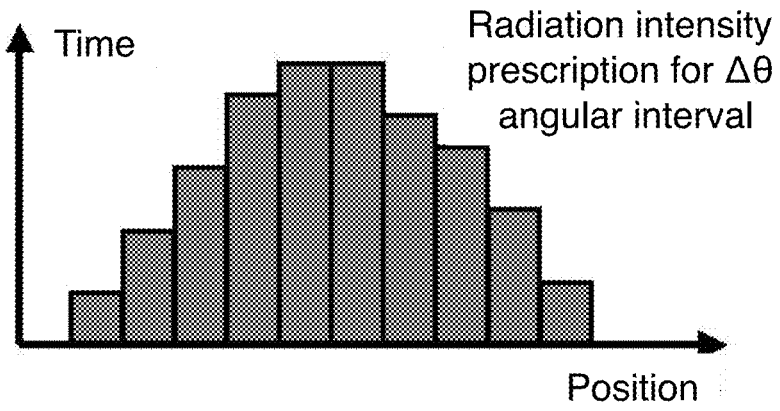
FIGS. 8A-8B illustrate leaf position and aperture weight optimization using the shortest path graph algorithm.
Figure 8B:
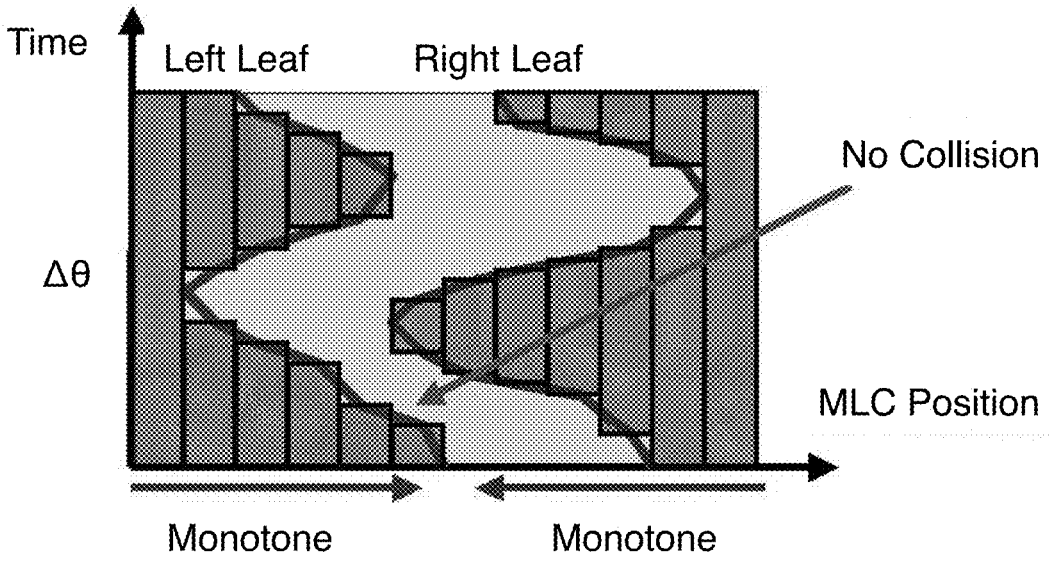

The above observation forms the basis for the following method:

First, for each given error bound, the intensity profile in every planning beam interval for each pair of MLC leaves is converted to a set of candidate sequences of leaf openings using a shortest path algorithm with minimized error subject to the error bound. These candidate sequences may differ from each other in the starting and/or ending leaf openings. FIG. 8B shows a candidate sequence for the intensity profile as shown in FIG. 8A with certain starting and ending leaf trajectory positions. The goal here is to construct a graph whose nodes are the candidate leaf trajectories. Each node will have a cost associated with it, which is the error of the trajectory when delivering its own profile. Two nodes from adjacent angular intervals are connected together if their transitions are smooth. A shortest path here yields an optimal single-arc plan. To improve the running time, one limits the number of candidate trajectories. e.g., by restricting the trajectories to be monotonic.

Second the sequences computed in the first step are connected together to form a single arc of leaf openings using a shortest path to ensure a smooth transition of the leaf positions between adjacent planning beam intervals while minimizing the total error incurred. Third, the single arcs for each pair of MLC leaves are then combined to form the final single-arc treatment plan.

Since the above method can compute a single-arc plan subject to an error bound, the method can compute a tradeoff between error and number of control points, or error and machine beam-on times.

EXAMPLE 4

Single Arc Sequencing

Figure 9A:
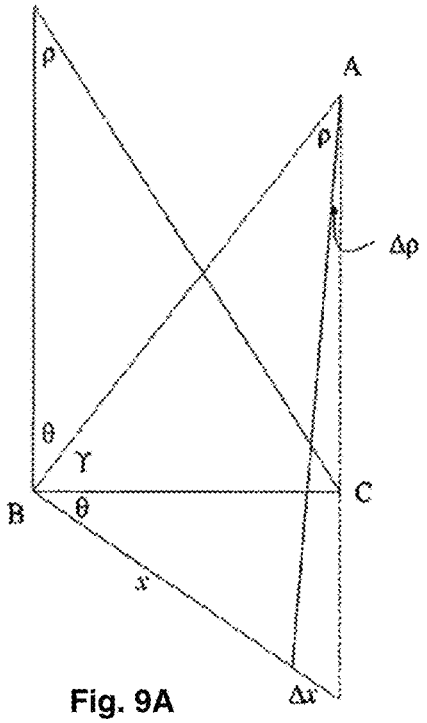
FIGS. 9A-9D illustrate field width adjustment on the right side (FIGS. 9A-9B) and on the left side (FIGS. 9C-9D).
Figure 9B:
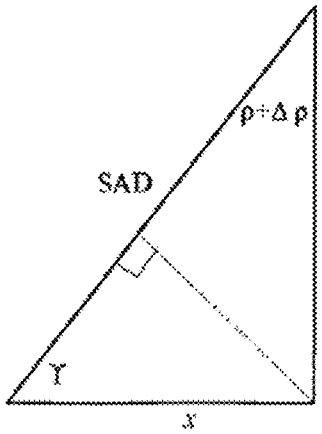

Note that up to this point, the apertures are all at the designated planning angle at the center of the planning interval. When we move the aperture to another angle a few degrees away, the dose will change slightly. To maintain the dose delivered to the target, the apertures are adjusted as follows:

In FIG. 9A, AB is the radiation source to rotational center i.e. isocenter, distance, and BC=x is the x coordinate of the right leaf. If the same opening is delivered at angle r away, the same opening will not be able to cover the same width of target as originally intended. To cover the same target width, the aperture needs to be enlarged by Dx. FIG. 9B omits DABC for clarity. From FIGS. 9A-9B, the following equation may be written:

$$\tan(\rho+\Delta\rho)=\frac{x\cdot\sin\gamma}{SAD-x\cdot\cos\gamma}.$$

This yields:

$$x+\Delta x=SAD\cdot\tan(\rho+\Delta\rho)=SAD\cdot\frac{x\cdot\sin\gamma}{SAD-x\cdot\cos\gamma}.$$

Substituting $$\gamma=\frac{\pi}{2}-\theta,$$

the following is obtained:

$$x-\Delta x=SAD\cdot\frac{x\cdot\sin\left(\frac{\pi}{2}-\theta\right)}{SAD+x\cdot\cos\left(\frac{\pi}{2}-\theta\right)}=SAD\cdot\frac{x\cdot\cos\theta}{SAD-x\cdot\sin\theta}.$$

Figure 9C:
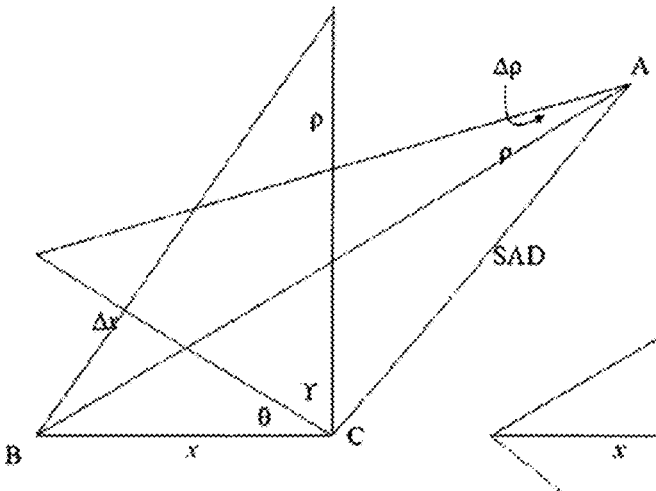
Figure 9D:
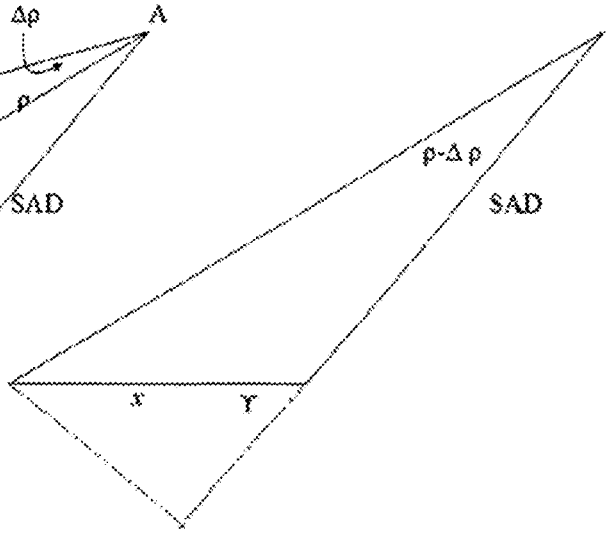

Similarly, the adjustment on the other side can be deduced. From FIGS. 9C-9D:

$$\tan(\rho-\Delta\rho)=\frac{x\cdot\sin\gamma}{SAD+x\cdot\cos\gamma}.$$

This gives:

$$x-\Delta x=SAD\cdot\tan(\rho-\Delta\rho)=SAD\cdot\frac{x\cdot\sin\gamma}{SAD+x\cdot\cos\gamma}.$$

Substituting $$\gamma=\frac{\pi}{2}-\theta,$$

the following is obtained:

$$x+\Delta x=SAD\cdot\frac{x\cdot\sin\left(\frac{\pi}{2}-\theta\right)}{SAD-x\cdot\cos\left(\frac{\pi}{2}-\theta\right)}=SAD\cdot\frac{x\cdot\cos\theta}{SAD+x\cdot\sin\theta}.$$

When the aperture is moved counterclockwise from the planned angle, r will be negative. Given these simple relationships, the new aperture widths can be set to provide the same coverage at the new angle as the original aperture provided at the planned angle. Alternatively or in addition to the above mentioned aperture shape adjustment for the apertures moved away from the planning angle, a simple aperture weight and shape optimization can be performed to further refine the single arc to deplete any potential rooms of improvement of the treatment plan quality.

EXAMPLE 5

Single Arc Painting for Cancer of Larynx

Figure 10A:
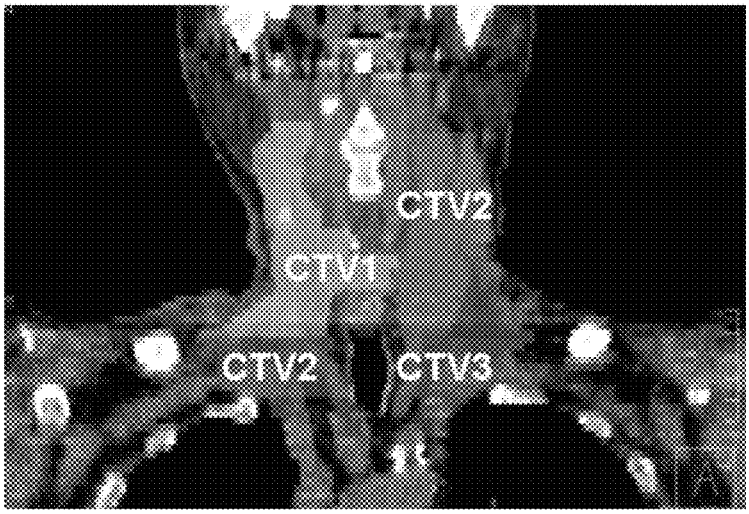
Figure 10B:
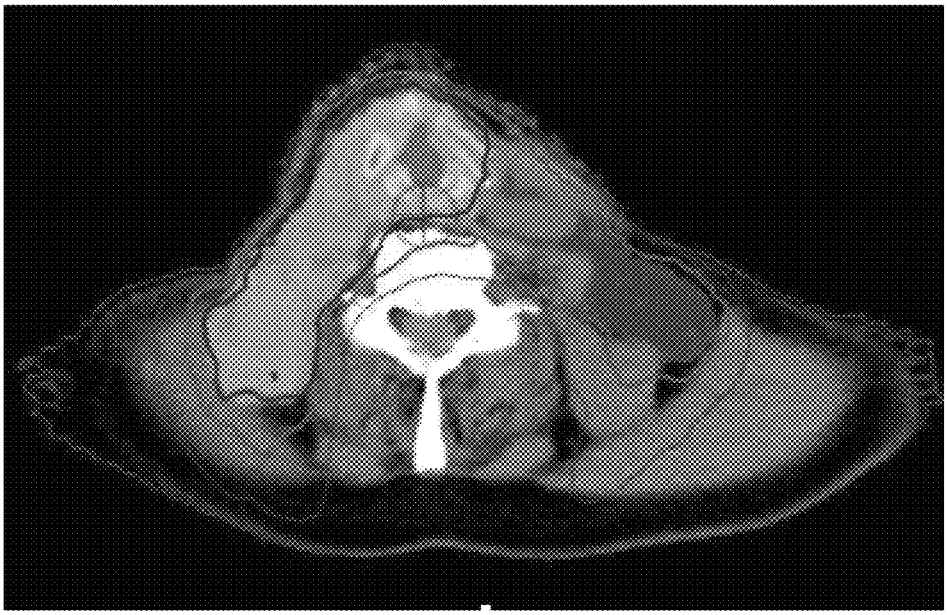

Sample plans were developed for several clinical cases. The plans were transferred to a Varian linear accelerator and delivered to a phantom. Comparison of the delivered and measured doses showed good agreement. One plan is for a larynx case with 3 targets, each with different dose specifications (FIG. 10A). FIG. 10B shows the dose distribution on a transverse slice at neck level resulting from the single-arc plan and FIG. 10C is the result of dose verification by delivering the single-arc plan to a phantom. Note that the phantom is different in size and shape from the patient and the calculated dose from the same plan is therefore also different.

THE FOLLOWING REFERENCES ARE CITED HEREIN

1. Bortfeld et al., Int J Rad Oncol Biol Phys, 28(3):723-730 (1994).

2. Boyer, A. & Yu, C., Seminars in Radiation Oncol 9(1): 48-59 (1999).
3. Mackie et al., Med Phys, 20(6):1709-19 (1993).
4. Yu et al., Phys. Med. Biol., 40:769-787 (1995).
5. Yu, C. X., Phys. Med. Biol., 40:1435-49, (1995).
6.Yu et al., Int J Radiat Oncol Biol Phys 53(2):453-63 (2002).
7. Cho, P. S. & Marks, R. J. II, Phys. Med. Biol, 45(2):429-440 (2000).
8. Earl et al., Phys. Med. Biol. 48(8):075-89 (2003).
9. Cameron, C., Phys Med. 50(18):4317-36 (2005).
10. Shepard et al., Med. Phys. 34(2):464-470 (February 2007).
11. Brahme, A., Int J Radiat Oncol Biol Phys. 49(2):327-37 (2001).
12. Shepard et al., Physics in Medicine and Biology, 45(1): 69-90 (1999).
13. Webb, S., Phys. Med. Biol. 39(12):2229-2246 (1994).

Any patents or publications mentioned in this specification are indicative of the level of those skilled in the art to which the invention pertains. Further, these patents and publications are incorporated by reference herein to the same extent as if each individual publication was specifically and individually incorporated by reference.

One skilled in the art would appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for designing a radiation treatment for a subject using single arc dose painting, comprising:

providing an unconstrained optimization map which supplies intensity profiles of densely-spaced radiation beams;

aligning each intensity profile to a pair of multiple leaf collimation (MLC) leaves;

applying a shortest path algorithm to convert each pair of MLC leaves to a set of leaf aperture sequences, said set of leaf aperture sequences forming a shortest path single arc thereof; [and]

connecting each single arc of leaf apertures to form a final treatment single arc path, thereby designing the single arc dose painting radiation treatment*; and*

*delivering a treatment dose of radiation to the subject during a single rotation along one or more of the final treatment single arc path.*

2. The method of claim 1, [further comprising:

delivering] *wherein the treatment dose is* a continuous dose of radiation *delivered* to the subject through each aperture during [a] *the* single rotation [along one or more final treatment single arc paths].

3. The method of claim 1, further comprising:

adjusting a shape of the aperture as a radiation dose delivery angle changes along the final treatment arc.

4. The method of claim 1, wherein the paths of more than one single arc are non-coplanar.

5. The method of claim 1, wherein the apertures sweep back and forth along the single arc path during delivery of the radiation dose.

6. The method of claim 1, wherein sequencing leaf apertures comprises one or more of a line segment approximation on component intensity profiles leaf position, weight optimization of apertures and optimization of leaf position and aperture weight.

7. The method of claim 1, wherein the leaf aperture sequences in each set have one or both of a different starting or ending leaf aperture.

8. The method of claim 7, wherein a starting and ending position of a leaf aperture trajectory are fixed.

9. The method of claim 1, wherein multiple leaf collimation is dynamic.

10. The method of claim 1, further comprising irradiating a tumor in a subject with the continuous dose of radiation through sets of multiple leaf collimation (MLC) aperture sequences during a single rotation along one or more of the treatment single arc paths.

11. The method of claim 10, further comprising:

adjusting a shape of the aperture as a radiation dose delivery angle changes along the treatment single arc path.

12. The method of claim 10, further comprising:

repeating the irradiation step during another rotation along the treatment single arc path(s).

13. The method of claim 10, wherein each set of MLC aperture sequences form a shortest path single arc thereof, said sets connected to form a shortest path treatment single arc.

14. A system for delivering radiation treatment using single arc dose painting, comprising *in a radiation delivery device*:

[a radiation source for generating a radiation beam;]

a multiple leaf collimator having a plurality of leafs for shaping [the] *a* radiation beam;

structure [for generating] *tangibly storing an algorithm enabling processor-executable instructions to generate* an unconstrained optimization map of intensity profiles of densely-spaced radiation beams;

structure [for aligning] *tangibly storing an algorithm enabling processor-executable instructions to align* each intensity profile to a pair of multiple leaf collimation (MLC) leaves; [and]

structure [for applying] *tangibly storing* a shortest path algorithm[, said shortest path algorithm converting] *enabling processor-executable instructions to convert* each pair of MLC leaves to a set of leaf aperture sequences forming a shortest path single arc thereof[, said shortest path algorithm] *and to* further [connecting] *connect* each single arc of leaf apertures to form a final treatment single arc effective for single arc dose painting*; and*

*a source of a dose of continuous radiation beams, varying radiation beams or both deliverable to the subject through each aperture during a single rotation along the final treatment single arc path.*

15. The system of claim 14, the shortest path algorithm further [adjusting] *enabling processor-executable instructions to adjust* a shape of the leaf aperture as a radiation dose delivery angle changes along the final treatment single arc.

16. The system of claim 14, wherein the shortest path algorithm [sequences] *enables processor-executable instructions to sequence* leaf apertures via one or more of a line segment approximation on component intensity profiles leaf position, weight optimization of apertures or optimization of leaf position and aperture weight.

17. The system of claim 14, wherein the multiple leaf collimator is dynamic.

[18. A computer-readable medium tangibly storing an algorithm to determine a final single arc path for a single arc dose painting radiation treatment, said algorithm enabling processor-executable instructions to:

convert pairs of multiple leaf collimation (MLC) leaves to sets of leaf aperture sequences that form a shortest path single arc thereof, said pairs of MLC leaves each aligned to an intensity profile of densely-spaced radiation beams; and connect each single arc of leaf apertures to form a final treatment single arc.]

[19. The computer-readable medium of claim 18, said algorithm further enabling instructions to:

adjust a shape of the leaf aperture as a radiation dose delivery angle changes along the final treatment single arc.]

[20. The computer-readable medium of claim 18, wherein the algorithm sequences leaf apertures via one or more of a line segment approximation on component intensity profiles leaf position, weight optimization of apertures or optimization of leaf position and aperture weight.]

*21. A method for designing a radiation treatment using a treatment arc comprising:*

*accessing an optimization map that supplies intensity profiles wherein at least some of the intensity profiles differ from one another with respect to a plurality of radiation beams;*

*aligning specific ones of the intensity profiles to corresponding pairs of multiple leaf collimator (MLC) leaves;*

*determining via a shortest path algorithm, for at least one of the pairs of MLC leaves, a plurality of leaf aperture sequences corresponding to angular intervals as each comprise a part of the treatment arc and combining the plurality of leaf aperture sequences over the angular intervals to form a treatment arc;*

*developing a final treatment arc using the treatment arc; and*

*delivering a dose of radiation to a subject based upon the leaf aperture sequences while traversing the final treatment arc; wherein the dose of radiation comprises a continuous dose of radiation, a varying dose of radiation or both while traversing the final treatment arc.*

*22. The method of claim 21 wherein the plurality of radiation beams comprises a plurality of densely-spaced radiation beams.*

*23. The method of claim 22 wherein the plurality of densely-spaced radiation beams are spaced no less than about ten degrees from one another.*

*24. The method of claim 21, wherein delivering a continuous dose of radiation to the subject comprises, at least in part, sweeping MLC apertures back and forth along the final treatment arc.*

*25. The method of claim 21 wherein determining a plurality of leaf aperture sequences comprises, at least in part, adjusting MLC aperture shapes as a radiation dose delivery angle changes along the treatment arc.*

*26. The method of claim 21 wherein determining the plurality of leaf aperture sequences comprises one or more of a line segment approximation on component intensity profiles leaf position, weight optimization of apertures, and optimization of leaf position and aperture weight.*

*27. The method of claim 21 wherein the plurality of leaf aperture sequences provide for dynamic multiple leaf collimation over the treatment arc.*

*28. The method of claim 21 wherein the optimization map comprises, at least in part, fluence distribution.*

*29. A method for designing a radiation treatment comprising:*

*accessing an optimization map that supplies intensity profiles wherein at least some of the intensity profiles differ from one another with respect to a plurality of radiation beams;*

*using the intensity profiles to develop a plurality of multiple leaf collimator aperture settings for use at various angles along a treatment arc;*

*determining via a shortest path algorithm a plurality of leaf aperture sequences from the plurality of multiple leaf collimator aperture settings;*

*using the plurality of leaf aperture sequences to form a radiation treatment plan to deliver a dose of radiation to a subject while dynamically adjusting a corresponding leaf collimator aperture based upon the plurality of leaf aperture sequences while traversing the treatment arc; and*

*delivering a dose of radiation to the subject while traversing the treatment arc using the radiation treatment plan; wherein the dose of radiation comprises a continuous dose of radiation, a varying dose of radiation or both while traversing the treatment arc via the radiation treatment plan.*

*30. The method of claim 29, wherein delivering the dose of radiation to the subject while dynamically adjusting a corresponding leaf collimator aperture comprises, at least in part, sweeping MLC apertures back and forth along the treatment arc.*

*31. The method of claim 29 wherein determining a plurality of leaf aperture sequences comprises, at least in part, adjusting MLC aperture shapes as a radiation dose delivery angle changes along the treatment arc.*

*32. A method for designing a radiation treatment using a treatment arc comprising:*

*accessing an optimization map that supplies intensity profiles wherein at least some of the intensity profiles differ from one another with respect to a plurality of radiation beams;*

*determining via a shortest path algorithm a plurality of multiple leaf collimator aperture sequences corresponding to angular intervals as each comprise a part of the treatment arc and forming the treatment arc based at least in part on the plurality of leaf aperture sequences over the angular intervals to form a treatment arc that provides for sweeping a multiple leaf collimator aperture back and forth along a treatment arc; and*

*delivering a dose of radiation to a subject while sweeping the multiple leaf collimator aperture back and forth along the treatment arc; wherein the dose of radiation comprises a continuous dose of radiation, a varying dose of radiation or both along the treatment arc during delivery.*

*33. The method of claim 32 wherein the plurality of radiation beams comprises a plurality of densely-spaced radiation beams.*

*34. The method of claim 33 wherein the plurality of densely-spaced radiation beams are spaced no less than about ten degrees from one another.*

*35. A planning system for developing a radiation treatment to be administered via a radiation source for generating a plurality of radiation beams and a multiple leaf collimator having a plurality of leafs for shaping the radiation beams, the planning system comprising:*

*structure tangibly storing an algorithm enabling processor-executed instructions to access an optimization map that supplies intensity profiles wherein at least*

*some of the intensity profiles differ from one another with respect to the plurality of radiation beams;*

*structure tangibly storing an algorithm enabling processor-executed instructions to align specific ones of the intensity profiles to corresponding pairs of multiple leaf collimator (MLC) leaves;*

*structure tangibly storing a shortest path algorithm enabling processor-executed instructions to:*

*determine, for at least one of the pairs of MLC leaves, a plurality of leaf aperture sequences corresponding to angular intervals as each comprise a part of the treatment arc;*

*combine the plurality of leaf aperture sequences over the angular intervals to form a treatment arc; and*

*develop a final treatment arc using the treatment arc;*

*a source of a continuous dose of radiation deliverable to a subject based upon the leaf aperture sequences while traversing the single treatment arc; and*

*a source of a varying dose of radiation deliverable to a subject based upon the leaf aperture sequences while traversing the single treatment arc.*

*36. The planning system of claim 35 wherein the plurality of radiation beams comprises a plurality of densely-spaced radiation beams.*

*37. The planning system of claim 36 wherein the plurality of densely-spaced radiation beams are spaced no less than about ten degrees from one another.*

*38. The planning system of claim 35, wherein the source of the continuous dose of radiation is configured to deliver the continuous dose of radiation by, at least in part, sweeping MLC apertures back and forth along the final treatment arc.*

*39. The planning system of claim 35 wherein the shortest path algorithm enables processor-executed instructions to, at least in part, adjust MLC aperture shapes as a radiation dose delivery angle changes along the treatment arc.*

*40. The planning system of claim 35 wherein the shortest path algorithm enables processor-executed instructions to use one or more of a line segment approximation on component intensity profiles leaf position, weight optimization of apertures, and optimization of leaf position and aperture weight.*

*41. The planning system of claim 35 wherein the plurality of leaf aperture sequences provide for dynamic multiple leaf collimation over the treatment arc.*

*42. The planning system of claim 35 wherein the optimization map comprises, at least in part, fluence distribution.*

*43. A planning system for developing a radiation treatment to be administered via a radiation source for generating a plurality of radiation beams and a multiple leaf collimator having a plurality of leafs for shaping the radiation beams, the planning system comprising:*

*structure tangibly storing an algorithm enabling processor-executed instructions to access an optimization map that supplies intensity profiles wherein at least some of the intensity profiles differ from one another with respect to a plurality of radiation beams;*

*structure tangibly storing an algorithm enabling processor-executed instructions to use the intensity profiles to develop a plurality of multiple leaf collimator aperture settings for use at various angles along a treatment arc;*

*structure tangibly storing a shortest path algorithm enabling processor-executed instructions to determine a plurality of leaf aperture sequences using the plurality of multiple leaf collimator aperture settings and to use the plurality of leaf aperture sequences to form a radiation treatment plan to deliver a dose of radiation to a subject while dynamically adjusting a corresponding leaf collimator aperture based upon the plurality of leaf aperture sequences while traversing the single treatment arc; and*

*a source of a continuous dose of radiation, a varying dose of radiation or both deliverable to the subject while traversing the single treatment arc.*

*44. The planning system of claim 43 wherein the shortest path algorithm enables processor-executed instructions to deliver the dose of radiation to the subject by, at least in part, sweeping MLC apertures back and forth along the single treatment arc.*

*45. The planning system of claim 43 wherein the algorithm for determining a plurality of leaf aperture sequences determines the plurality of leaf aperture sequences by, at least in part, adjusting MLC aperture shapes as a radiation dose delivery angle changes along the treatment arc.*

*46. A planning system for developing a radiation treatment to be administered via a radiation source for generating a plurality of radiation beams and a multiple leaf collimator having a plurality of leafs for shaping the radiation beams, the planning system comprising:*

*structure tangibly storing an algorithm enabling processor-executed instructions to access an optimization map that supplies intensity profiles wherein at least some of the intensity profiles differ from one another with respect to a plurality of radiation beams;*

*structure tangibly storing a shortest path algorithm enabling processor-executed instructions to:*

*determine a plurality of multiple leaf collimator aperture sequences corresponding to angular intervals as each comprise a part of the treatment arc; and*

*form the treatment arc based at least in part on the plurality of leaf aperture sequences over the angular intervals to form a treatment arc that provides for sweeping a multiple leaf collimator aperture back and forth along the treatment arc; and*

*a source of a continuous dose of radiation, a varying dose of radiation or both deliverable to a subject while sweeping the multiple leaf collimator aperture back and forth along the treatment arc.*

*47. The planning system of claim 46 wherein the plurality of radiation beams comprises a plurality of densely-spaced radiation beams.*

*48. The planning system of claim 47 wherein the plurality of densely-spaced radiation beams are spaced no less than about ten degrees from one another.*

* * * * *